US012569222B2

(12) United States Patent
Hutchins et al.

(10) Patent No.: US 12,569,222 B2
(45) Date of Patent: Mar. 10, 2026

(54) INTERFACE DEVICES, SYSTEMS AND METHODS FOR MULTIMODAL PROBES

(71) Applicant: LightLab Imaging, Inc., Westford, MA (US)

(72) Inventors: Christopher Hutchins, Londonderry, NH (US); Michael Atlas, Arlington, MA (US); Alexander Ship, Needham, MA (US)

(73) Assignee: LightLab Imaging, Inc., Westford, MA (US)

( * ) Notice: Subject to any disclaimer, the term of this patent is extended or adjusted under 35 U.S.C. 154(b) by 121 days.

(21) Appl. No.: 18/415,303

(22) Filed: Jan. 17, 2024

(65) Prior Publication Data

US 2024/0164748 A1 May 23, 2024

Related U.S. Application Data

(60) Continuation of application No. 17/009,991, filed on Sep. 2, 2020, now Pat. No. 12,127,881, which is a
(Continued)

(51) Int. Cl.
*A61B 8/00* (2006.01)
*A61B 5/00* (2006.01)
*A61B 8/12* (2006.01)

(52) U.S. Cl.
CPC .......... *A61B 8/4416* (2013.01); *A61B 5/0035* (2013.01); *A61B 5/0066* (2013.01);
(Continued)

(58) Field of Classification Search
CPC .................................................. A61B 8/4416
See application file for complete search history.

(56) References Cited

U.S. PATENT DOCUMENTS 5,039,193 A 8/1991 Snow et al.
5,076,279 A 12/1991 Arenson et al.
(Continued)

FOREIGN PATENT DOCUMENTS

EP 2484288 A1 8/2012
JP S61103436 A 5/1986
(Continued)

OTHER PUBLICATIONS

Extended Search Report for Application No. PCT/US2013024620, mailed from European Patent Office on Jun. 21, 2016 (12 pages).
(Continued)

*Primary Examiner* — Joseph M Santos Rodriguez
(74) *Attorney, Agent, or Firm* — Lerner David LLP

(57) ABSTRACT

In one aspect, the invention relates to one or more rotatable elements and one or more stationary element such that the elements are arranged along a common axis of rotation co-linear with or substantially parallel to an optical path. The optical path is a portion of a sample arm of an interferometer. Further, the rotatable and stationary elements are configured to couple electrical signals and optical signals between a data collection probe and an interface unit or other component of an imaging system. In one embodiment, the data collection probe is a combination ultrasound and OCT probe. In one aspect, the invention relates to a rotary joint in which the optical fiber and a fiber optic rotary joint lie in the center of one or more conductive elements of an electrical rotary joint which are annularly disposed around one or both of the optical fiber and optical rotary joint.

20 Claims, 20 Drawing Sheets

Related U.S. Application Data division of application No. 13/758,591, filed on Feb. 4, 2013, now Pat. No. 10,792,012.

(60) Provisional application No. 61/727,997, filed on Nov. 19, 2012, provisional application No. 61/728,006, filed on Nov. 19, 2012.

(52) U.S. Cl.
CPC .......... *A61B 5/0084* (2013.01); *A61B 5/6852* (2013.01); *A61B 8/12* (2013.01); *A61B 2562/0204* (2013.01); *A61B 2562/0233* (2013.01)

(56) References Cited

U.S. PATENT DOCUMENTS

| | | | |
|---|---|---|---|
| 5,274,551 A | 12/1993 | Corby, Jr. |
| 5,293,873 A | 3/1994 | Fang |
| 5,313,949 A | 5/1994 | Yock |
| 5,321,501 A | 6/1994 | Swanson et al. |
| 5,335,662 A | 8/1994 | Kimura et al. |
| 5,350,377 A | 9/1994 | Winston et al. |
| 5,459,570 A | 10/1995 | Swanson et al. |
| 5,465,147 A | 11/1995 | Swanson |
| 5,503,155 A | 4/1996 | Salmon et al. |
| 5,509,093 A | 4/1996 | Miller et al. |
| 5,582,178 A | 12/1996 | Yock |
| 5,588,434 A | 12/1996 | Fujimoto |
| 5,619,368 A | 4/1997 | Swanson |
| 5,748,598 A | 5/1998 | Swanson et al. |
| 5,784,352 A | 7/1998 | Swanson et al. |
| 5,830,145 A | 11/1998 | Tenhoff |
| 5,965,355 A | 10/1999 | Swanson et al. |
| 6,036,648 A | 3/2000 | White et al. |
| 6,111,645 A | 8/2000 | Tearney et al. |
| 6,129,667 A | 10/2000 | Dumoulin et al. |
| 6,134,003 A | 10/2000 | Tearney et al. |
| 6,160,826 A | 12/2000 | Swanson et al. |
| 6,191,862 B1 | 2/2001 | Swanson et al. |
| 6,217,527 B1 | 4/2001 | Selmon et al. |
| 6,226,546 B1 | 5/2001 | Evans |
| 6,265,792 B1 | 7/2001 | Granchukoff |
| 6,282,011 B1 | 8/2001 | Tearney et al. |
| 6,299,622 B1 | 10/2001 | Snow et al. |
| 6,421,164 B2 | 7/2002 | Tearney et al. |
| 6,423,002 B1 | 7/2002 | Hossack |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,585,660 B2 | 7/2003 | Dorando et al. |
| 6,612,304 B1 | 9/2003 | Cise et al. |
| 6,706,004 B2 | 3/2004 | Tearney et al. |
| 6,847,454 B2 | 1/2005 | Crowley et al. |
| 6,879,851 B2 | 4/2005 | McNamara et al. |
| 6,891,984 B2 | 5/2005 | Petersen et al. |
| 6,947,787 B2 | 9/2005 | Webler |
| 7,134,994 B2 | 11/2006 | Alpert et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,366,562 B2 | 4/2008 | Dukesherer et al. |
| 7,414,779 B2 | 8/2008 | Huber et al. |
| 7,415,049 B2 | 8/2008 | Flanders et al. |
| 7,477,763 B2 | 1/2009 | Willis et al. |
| 7,605,681 B2 | 10/2009 | Wobben |
| 7,621,874 B2 | 11/2009 | Romley et al. |
| 7,625,366 B2 | 12/2009 | Atlas |
| 7,729,745 B2 | 6/2010 | Maschke |
| 7,751,865 B2 | 7/2010 | Jascob et al. |
| 7,785,261 B2 | 8/2010 | Maschke |
| 7,813,609 B2 | 10/2010 | Petersen et al. |
| 7,818,044 B2 | 10/2010 | Dukesherer et al. |
| 7,822,464 B2 | 10/2010 | Maschke et al. |
| 7,840,253 B2 | 11/2010 | Tremblay et al. |
| 7,848,791 B2 | 12/2010 | Schmitt et al. |
| 7,916,387 B2 | 3/2011 | Schmitt |
| 7,935,060 B2 | 5/2011 | Schmitt et al. |
| 8,100,833 B2 | 1/2012 | Hirota |
| 8,116,605 B2 | 2/2012 | Petersen et al. |
| 8,162,834 B2 | 4/2012 | Feldman et al. |
| 8,206,377 B2 | 6/2012 | Petroff |
| 8,214,010 B2 | 7/2012 | Courtney et al. |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,548,567 B2 | 10/2013 | Maschke et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,660,389 B2 | 2/2014 | Jono et al. |
| 8,687,201 B2 | 4/2014 | Adler |
| 8,786,336 B1 | 7/2014 | Schmitt |
| 8,831,321 B1 | 9/2014 | Elbasiony |
| 8,948,228 B2 | 2/2015 | Adler |
| 8,953,911 B1 | 2/2015 | Xu et al. |
| 2001/0031919 A1 | 10/2001 | Strommer et al. |
| 2002/0019644 A1 | 2/2002 | Hastings et al. |
| 2002/0049375 A1 | 4/2002 | Strommer et al. |
| 2002/0161351 A1 | 10/2002 | Samson et al. |
| 2003/0077043 A1 | 4/2003 | Hamm et al. |
| 2003/0114869 A1 | 6/2003 | Nash et al. |
| 2005/0025797 A1 | 2/2005 | Wang et al. |
| 2005/0043618 A1 | 2/2005 | Mansouri-Ruiz |
| 2005/0075574 A1 | 4/2005 | Furnish et al. |
| 2005/0101859 A1 | 5/2005 | Maschke |
| 2005/0113685 A1 | 5/2005 | Maschke et al. |
| 2005/0149002 A1 | 7/2005 | Wang et al. |
| 2005/0162237 A1 | 7/2005 | Yamashita |
| 2005/0201662 A1 | 9/2005 | Petersen et al. |
| 2005/0261582 A1 | 11/2005 | Becker et al. |
| 2005/0279914 A1 | 12/2005 | Dimsdale et al. |
| 2005/0288582 A1 | 12/2005 | Yu et al. |
| 2006/0005861 A1 | 1/2006 | Lynn |
| 2006/0025677 A1 | 2/2006 | Verard et al. |
| 2006/0058614 A1 | 3/2006 | Tsujita |
| 2006/0058622 A1 | 3/2006 | Tearney et al. |
| 2006/0084867 A1 | 4/2006 | Tremblay et al. |
| 2006/0093276 A1 | 5/2006 | Bouma et al. |
| 2006/0095065 A1 | 5/2006 | Tanimura et al. |
| 2006/0100489 A1 | 5/2006 | Pesach et al. |
| 2006/0116577 A1 | 6/2006 | DeWitt |
| 2006/0173299 A1 | 8/2006 | Romley et al. |
| 2006/0241465 A1 | 10/2006 | Huennekens et al. |
| 2006/0241572 A1 | 10/2006 | Zhou |
| 2006/0247529 A1 | 11/2006 | Rose et al. |
| 2007/0038061 A1 | 2/2007 | Huennekens et al. |
| 2007/0060822 A1 | 3/2007 | Alpert et al. |
| 2007/0100239 A1 | 5/2007 | Nair et al. |
| 2007/0167833 A1 | 7/2007 | Redel et al. |
| 2007/0232933 A1 | 10/2007 | Gille et al. |
| 2007/0243137 A1 | 10/2007 | Hainfeld |
| 2008/0114254 A1 | 5/2008 | Matcovitch et al. |
| 2008/0123911 A1 | 5/2008 | Lam et al. |
| 2008/0161696 A1 | 7/2008 | Schmitt et al. |
| 2008/0171937 A1 | 7/2008 | Dukesherer et al. |
| 2008/0177138 A1 | 7/2008 | Courtney et al. |
| 2008/0177139 A1 | 7/2008 | Courtney et al. |
| 2008/0177183 A1 | 7/2008 | Courtney et al. |
| 2008/0180683 A1 | 7/2008 | Kemp |
| 2008/0269572 A1 | 10/2008 | Kanz et al. |
| 2008/0287795 A1 | 11/2008 | Klingensmith et al. |
| 2009/0003031 A1 | 1/2009 | Kimura |
| 2009/0018393 A1 | 1/2009 | Dick et al. |
| 2009/0025398 A1 | 1/2009 | Muller et al. |
| 2009/0030312 A1 | 1/2009 | Hadjicostis |

(56) References Cited

U.S. PATENT DOCUMENTS

| | | | |
|---|---|---|---|
| 2009/0043191 A1 | 2/2009 | Castella et al. | |
| 2009/0174931 A1 | 7/2009 | Huber et al. | |
| 2009/0195514 A1 | 8/2009 | Glynn et al. | |
| 2009/0244545 A1 | 10/2009 | Toida | |
| 2009/0253989 A1 | 10/2009 | Caplan et al. | |
| 2009/0264768 A1 | 10/2009 | Courtney et al. | |
| 2009/0270737 A1 | 10/2009 | Thornton | |
| 2009/0299195 A1 | 12/2009 | Muller et al. | |
| 2009/0306520 A1 | 12/2009 | Schmitt et al. | |
| 2010/0076320 A1 | 3/2010 | Petersen et al. | |
| 2010/0152590 A1 | 6/2010 | Moore et al. | |
| 2010/0160788 A1 | 6/2010 | Davies et al. | |
| 2010/0210939 A1 | 8/2010 | Hartmann et al. | |
| 2010/0234736 A1 | 9/2010 | Corl | |
| 2010/0249588 A1 | 9/2010 | Knight | |
| 2010/0274124 A1 | 10/2010 | Jascob et al. | |
| 2011/0025148 A1 | 2/2011 | Fukunaga et al. | |
| 2011/0058178 A1 | 3/2011 | Tearney et al. | |
| 2011/0071404 A1 | 3/2011 | Schmitt et al. | |
| 2011/0098572 A1 | 4/2011 | Chen et al. | |
| 2011/0101207 A1 | 5/2011 | Schmitt | |
| 2011/0137399 A1 | 6/2011 | Chomas et al. | |
| 2011/0157686 A1 | 6/2011 | Huber et al. | |
| 2011/0164255 A1 | 7/2011 | Konno et al. | |
| 2011/0172511 A1 | 7/2011 | Schmitt et al. | |
| 2011/0178398 A1 | 7/2011 | Tearney et al. | |
| 2011/0178409 A1* | 7/2011 | Harris | G02B 23/2423 |
| | | | 359/389 |
| 2011/0190586 A1 | 8/2011 | Kemp | |
| 2011/0228280 A1 | 9/2011 | Schmitt et al. | |
| 2011/0251487 A1 | 10/2011 | Magnin et al. | |
| 2012/0069348 A1 | 3/2012 | Jono et al. | |
| 2012/0108979 A1 | 5/2012 | Franklin et al. | |
| 2012/0236883 A1 | 9/2012 | Adler | |
| 2012/0238869 A1 | 9/2012 | Schmitt et al. | |
| 2012/0250028 A1 | 10/2012 | Schmitt et al. | |
| 2012/0253185 A1 | 10/2012 | Furuichi | |
| 2012/0283564 A1 | 11/2012 | Ebbini et al. | |
| 2012/0283569 A1 | 11/2012 | Ciompi et al. | |
| 2012/0310081 A1 | 12/2012 | Adler et al. | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0051728 A1 | 2/2013 | Petroff et al. | |
| 2013/0072805 A1 | 3/2013 | Schmitt et al. | |
| 2013/0310698 A1 | 11/2013 | Judell et al. | |
| 2014/0018669 A1 | 1/2014 | Xu | |
| 2014/0024931 A1 | 1/2014 | Winston et al. | |
| 2014/0094697 A1 | 4/2014 | Petroff et al. | |
| 2014/0114182 A1 | 4/2014 | Petersen et al. | |
| 2014/0142427 A1 | 5/2014 | Petroff | |
| 2014/0142432 A1 | 5/2014 | Hutchins et al. | |
| 2014/0142436 A1 | 5/2014 | Hutchins et al. | |
| 2014/0187929 A1 | 7/2014 | Schmitt et al. | |
| 2014/0218742 A1 | 8/2014 | Adler | |
| 2014/0249407 A1 | 9/2014 | Adler et al. | |
| 2014/0257087 A1 | 9/2014 | Elbasiony et al. | |
| 2014/0267038 A1 | 9/2014 | Adler et al. | |
| 2014/0268167 A1 | 9/2014 | Friedman et al. | |
| 2014/0270436 A1 | 9/2014 | Dascal et al. | |
| 2014/0276011 A1 | 9/2014 | Schmitt et al. | |
| 2014/0276020 A1 | 9/2014 | Hutchins et al. | |
| 2014/0309536 A1 | 10/2014 | Douk et al. | |
| 2014/0379269 A1 | 12/2014 | Schmitt | |
| 2015/0119707 A1 | 4/2015 | Schmitt | |
| 2015/0153157 A1 | 6/2015 | Schmitt et al. | |
| 2015/0192405 A1 | 7/2015 | Schmitt | |
| 2015/0297373 A1 | 10/2015 | Schmitt et al. | |

FOREIGN PATENT DOCUMENTS

| | | |
|---|---|---|
| JP | H05-329156 A | 12/1993 |
| JP | H09168538 A | 6/1997 |
| JP | H1156752 A | 3/1999 |
| JP | H11276484 A | 10/1999 |
| JP | 2002153472 A | 5/2002 |
| JP | 2002528205 A | 9/2002 |
| JP | 2004290548 A | 10/2004 |
| JP | 2004357901 A | 12/2004 |
| JP | 2005-095624 A | 4/2005 |
| JP | 2005150198 A | 6/2005 |
| JP | 2005-533533 A | 11/2005 |
| JP | 2006006958 A | 1/2006 |
| JP | 2006280449 A | 10/2006 |
| JP | 2008510586 A | 4/2008 |
| JP | 2008521022 A | 6/2008 |
| JP | 2008191022 A | 8/2008 |
| JP | 2009101177 A | 5/2009 |
| JP | 2009172118 A | 8/2009 |
| JP | 2009183416 A | 8/2009 |
| JP | 2009183417 A | 8/2009 |
| JP | 2010508973 A | 3/2010 |
| JP | 2010516304 A | 5/2010 |
| JP | 2010516305 A | 5/2010 |
| JP | 2010-125273 A | 6/2010 |
| JP | 2011072597 A | 4/2011 |
| JP | 2011512961 A | 4/2011 |
| JP | 2011-516865 A | 5/2011 |
| JP | 2011-519689 A | 7/2011 |
| JP | 2012510885 A | 5/2012 |
| JP | 2012-521852 A | 9/2012 |
| JP | 2012520127 A | 9/2012 |
| JP | 2012210381 A | 11/2012 |
| JP | 2013541389 A | 11/2013 |
| JP | 2016073723 A | 5/2016 |
| WO | 2008057573 A2 | 5/2008 |
| WO | 2008086613 A1 | 7/2008 |
| WO | 2008086615 A1 | 7/2008 |
| WO | 2008086616 A1 | 7/2008 |
| WO | 2009009802 A1 | 1/2009 |
| WO | 2009137659 A1 | 11/2009 |
| WO | 2010029935 A1 | 3/2010 |
| WO | 2010/104775 A2 | 9/2010 |
| WO | 2010137375 A1 | 12/2010 |
| WO | 2011/039955 A1 | 4/2011 |
| WO | 2012/061940 A1 | 5/2012 |
| WO | 2012091903 A1 | 7/2012 |
| WO | 2013033592 A1 | 3/2013 |
| WO | 2014077871 A2 | 5/2014 |

OTHER PUBLICATIONS

JP 2018-108342, Notice of Reason(s) for Rejection, dated Mar. 19, 2019.

Search Report for Japanese Patent Application No. 2015-543025 dated Nov. 14, 2016. 12 pgs.

Office Action for Japanese Patent Application No. 2015-543025 dated Dec. 13, 2016. 5 pgs.

Search Report for Japanese Patent Application No. 2019-210995 dated Aug. 11, 2020. 9 pgs.

Extended European Search Report for Application No. 23218841.7 dated Apr. 9, 2024 (6 pages).

Search Report for Japanese Patent Application No. 2015-543026 dated Nov. 16, 2016. 15 pgs.

Office Action for Japanese Patent Application No. 2015-543026 dated Nov. 29, 2016. 3 pgs.

Search Report for Japanese Patent Application No. 2017-246030 dated Aug. 21, 2018. 8 pgs.

Search Report for Japanese Patent Application No. 2019-186748 dated Jul. 16, 2020. 9 pgs.

J. A. Ketterling, O. Aristizabal and D. H. Turnbull, "High-frequency piezopolymer transducers with a copper-clad polyimide backing layer," in IEEE Transactions on Ultrasonics, Ferroelectrics, and Frequency Control, vol. 53, No. 7, pp. 1376-1380, Jul. 2006, doi: 10.1109/TUFFC.2006.1665086. 5 pgs.

Li, Xiang et al. "High-resolution coregistered intravascular imaging with integrated ultrasound and optical coherence tomography probe." Applied physics letters vol. 97,13 (Sep. 2010): 133702. doi: 10.1063/1.3493659. 4 pgs.

(56)        References Cited

OTHER PUBLICATIONS

English translation of Japanese Office Action for Japanese Patent Application No. 2017-246030 mailed Oct. 23, 2018 (7 pages).

Yin et al., "Novel combined miniature optical coherence tomography ultrasound probe for in vivo intravascular imaging", J. Biomed Optics, Jun. 2011 vol. 16(6), 4 pages.

Bezerra et al., "Intracoronary Optical Coherence Tomography: A Comprehensive Review", JACC: Cardiovascular interventions, (2009) 2:11, pp. 1035-1046.

Herickhoff et al., "Dual-mode IVUS Transducer for Image-Guided Brain Therapy: Preliminary Experiments", Ultrasound Med Biol. Oct. 2011; 37(10): 1667-1676.

Mao et al. "Fiber lenses for ultra-small probes used in optical coherent tomography", J. Biomedical Science and Engineering, 2010, 3, 27-34.

Prati et al., "Intracoronary optical coherence tomography, basic theory and image acquisition techniques", Int. J. Cardiovasc. Imaging (2011) 27: 251-258.

Tsai et al., "Piezoelectric-transducer-based miniature catheter for ultrahigh-speed endoscopic optical coherence tomography", Biomedical Optics Express, 2:8, Aug. 1, 2011, pp. 2438-2448.

Extended European Search Report for Application No. PCT/US2013/024628 mailed Jun. 16, 2016 (7 pages).

International Search Report and the Written Opinion of the International Searching Authority for International Application No. PCT/US2013/024620 issued on Apr. 5, 2013 (14 pgs.).

Li et al., "Hybrid Intravascular Ultrasound and Optical Coherence Tomography Catheter for Imaging of Coronary Atherosclerosis", Catherization and Cardiovascular Interventions 81:494-507 (2013).

Bourantas et al., "Hybrid Intravascular Imaging—Current Applications and Prospective Potential in the Study of Coronary Athersclerosis", JACC 61:13 1369-1378 (2013).

Prati et al., "Expert review document part 2: methodology, terminology and clinical applications of optical coherence tomography for the assessment of interventional procedures", European Heart Journal, May 31, 2012 (pp. 1-10).

Yang et al., "A Dual-Modality Probe Utilizing Intravascular Ultrasound and Optical Coherence Tomography for Intravascular Imaging Applications", IEEE Transactions of Ultrasonics, Ferroelectrics, and Frequency Control 57:12 2839-2843 (2010).

Translation of Office Action mailed from Japanese Patent Office on Oct. 22, 2013 for Japanese Patent Application No. 2009-536291 (4 pages).

Translation of Office Action mailed from Japanese Patent Office on Oct. 22, 2013 for Japanese Patent Application No. 2013-131070 (4 pages).

International Search Report and the Written Opinion of the International Searching Authority for International Application No. PCT/US2007/023493 issued on Apr. 23, 2008 (17 pages).

European Office Action from EP Appl. No. 23218841.7, dated Dec. 18, 2024, pp. 1-7.

Communication under Rule 71(3) EPC for Application No. 23218841.7 dated May 26, 2025. 59 pgs.

* cited by examiner

INTERFACE DEVICES, SYSTEMS AND METHODS FOR MULTIMODAL PROBES

CROSS-REFERENCE TO RELATED APPLICATIONS

This application is a continuation of U.S. patent application Ser. No. 17/009,991, filed on Sep. 2, 2020, which is a divisional of U.S. patent application Ser. No. 13/758,591, filed on Feb. 4, 2013, now U.S. Pat. No. 10,792,012, which claims priority to and the benefit of U.S. Patent Provisional Patent Application No. 61/727,997, filed on Nov. 19, 2012, and U.S. Provisional Patent Application 61/728,006, filed on Nov. 19, 2012, the disclosures of which are incorporated herein by reference.

FIELD OF THE INVENTION

The invention relates generally to the field of intravascular ultrasound (IVUS) and optical coherence tomography (OCT), and more specifically to OCT and IVUS combination data collection probes and related interface units for such probes.

BACKGROUND

Coronary artery disease is one of the leading causes of death worldwide. The ability to better diagnose, monitor, and treat coronary artery diseases can be of life saving importance. Optical coherence tomography (OCT) is a catheter-based imaging modality that uses light to penetrate a sample such as blood vessel walls and generate images of the same. These images are valuable for the study of the vascular wall architecture and blood vessel geometry. Intravascular ultrasound (IVUS) is another imaging technology that can be used to image a blood vessel. The images generated using OCT are of a higher resolution and more clearly depict structures such as plaques and stent struts as well as other objects and characteristics of interest when imaging a blood vessel.

Conversely, IVUS has a better penetration depth relative to OCT. IVUS can typically penetrate tissue, such as a vessel wall, within the range of about 4 mm to about 8 mm. Unfortunately, IVUS images are typically of a lower resolution, which can make interpreting them more challenging. OCT has a shorter penetration depth and can typically penetrate tissue, such as a vessel wall, within the range of about 2 mm to about 3 mm. Given the respective advantages of OCT and IVUS in terms of imaging depth and otherwise, a need exists to develop systems that integrate these two imaging modalities such that their respective advantages may be combined without their associated disadvantages.

The present invention addresses these needs and others.

SUMMARY OF INVENTION

In one aspect, the invention relates to a patient interface unit or device (PIU) configured to interface with a data collection probe. In one embodiment, the data collection probe includes a probe tip configured to collect optical data and ultrasound data with respect to a sample such as a blood vessel. The data collection probe is disposable in one embodiment. The PIU is configured to relay optically collected data (in an optical format or a converted format) and electrically collected ultrasound data to one or more receivers. One or more of the rotatable components of the PIU are configured to rotate an optical fiber and the probe tip. In one embodiment, the probe tip includes a beam director and an acoustic wave generator such as a transducer.

In one embodiment, the PIU includes a connector and a sacrificial connector joint. In one embodiment, the connector includes a counterbalance sized to match the mass of an electrical contact or connection disposed opposite the connector. The counterbalance and the electrical contact are disposed inside the connector in one embodiment. The sacrificial connector joint is configured to permit replacing an electrical connection to the PIU without electrically rewiring the PIU or replacing an optical fiber disposed in the PIU.

In one aspect, the invention relates to an interface device. The interface device includes a cover; an aperture defined by the cover; a stationary section of a sample arm of an interferometer disposed within the cover and comprising a stationary optical fiber section having an endface; a first rotatable connector defining a first hole, the first hole positioned in alignment relative to the aperture and disposed within the cover; a sacrificial connector; a second rotatable connector defining a second hole, the first second positioned in alignment relative to the aperture, wherein the first rotatable connector and the second rotatable connector sandwich the sacrificial connector and; a first motor disposed within the cover, the first motor configure to rotate the second rotatable connector.

In one embodiment, the first rotatable connector includes a first half and a second half, wherein the first half comprises an electrical contact, wherein the second half comprises a counterbalance. The interface device can further include an electrical signal coupling subsystem comprising a rotatable transformer component and a stationary transformer component. In one embodiment, the interface device includes an optical signal coupling subsystem which includes a rotatable optical component and a stationary optical component. The interface device can further include an optical connector disposed within the rotatable optical connector. The interface device can further include an elongate probe connector comprising one or more posts extending therefrom. The interface device can further include a rotatable section of a sample arm of an interferometer aligned with the aperture.

In part, one aspect of the invention relates generally to a coupler for coupling electrical and optical lines of a combination IVUS and OCT probe to a patient interface device. In one aspect, the invention relates to one or more rotatable elements and one or more stationary element such that the elements are arranged along a common axis of rotation co-linear with or substantially parallel to an optical path. The optical path is a portion of a sample arm of an interferometer. Further, the rotatable and stationary elements are configured to couple electrical signals and optical signals between a data collection probe and an interface unit or other component of an imaging system. In one embodiment, the data collection probe is a combination ultrasound and OCT probe. In one aspect, the invention relates to a rotary joint in which the optical fiber and a fiber optic rotary joint lie in the center of one or more conductive elements of an electrical rotary joint which are annularly disposed around one or both of the optical fiber and optical rotary joint.

In one aspect, the invention relates to a combination rotary joint in which the optical fiber and fiber optic rotary joint lies in the center of the combination rotary joint and the electrical wires and the electrical rotary joint are annularly disposed around the fiber/fiber optic rotary joint. In one embodiment, the electrical wires are disposed in one or more coils. In one embodiment, a first coil and a second coil are used. The number of turns in the first coil and the second coil are specified by a ratio of C1:C2 to each other. In one embodiment, C1:C2 is about 1:about 1. In another embodiment, C1:C2 is about 2:about 1. In another embodiment the ratio of C1:C2 is about 4:about 1. In another embodiment the ratio of C1:C2 ranges from greater than or equal to about 1 to about 10. In one embodiment, the ratio C1:C2 is selected to adjust for impedance mismatch. In one embodiment, the ratio C1:C2 is selected to increase the signal amplitude of voltage resulting from the reflection of the ultrasound signal from tissue.

In one aspect, the invention relates to a catheter-based data collection probe that includes one or more sheaths. An optical fiber is slidably disposed in one such sheath and is helically wrapped with electrical conductors. The electrical conductors can be disposed within or encased by a torque wire.

In one aspect, the invention relates to a combination catheter pullback section which includes a plurality of subsections or components. In one embodiment, such a subsection or component can include one or more of a flexible catheter body, a transition catheter purge section, a breakaway joint such a torque limiter, a rigid unsupported pullback section, and an imaging core connector.

In one aspect, the invention relates to a connection system configured to connect and release a data collection probe to an interface device such as a patient interface unit or PIU. In one embodiment, the connection system includes a connector which utilizes a single twist to engage automatic connection. In one embodiment, the PIU side of the connector includes a double ended sacrificial interconnect. In one embodiment, a sterile plastic bag having an access port is used to drape the PIU.

In one aspect, the invention relates to a combination PIU in which electrical motor noise from a PWM (Pulse Width Modulator), used to control the speed of the motor, is reduced by filtering the edges of the driving pulse waves.

In one aspect, the invention relates to an interface device that includes a cover; an aperture defined by the cover; a stationary section of a sample arm of an interferometer disposed within the cover and includes a stationary optical fiber section having an endface; a first rotatable connector defining a first hole, the first hole positioned in alignment relative to the aperture and disposed within the cover; a sacrificial connector; a second rotatable connector defining a second hole, the first second positioned in alignment relative to the aperture, wherein the first rotatable connector and the second rotatable connector sandwich the sacrificial connector and; a first motor disposed within the cover, the first motor configure to rotate the second rotatable connector.

In one embodiment, the first rotatable connector includes a first half and a second half, wherein the first half comprises an electrical contact, wherein the second half comprises a counterbalance. In one embodiment, the interface device further includes an electrical signal coupling subsystem includes a rotatable transformer component and a stationary transformer component. In one embodiment, the interface device further includes an optical signal coupling subsystem includes a rotatable optical component and a stationary optical component. In one embodiment, the interface device further includes an optical connector disposed within the rotatable optical connector. In one embodiment, the interface device further includes an elongate probe connector includes one or more posts extending therefrom. In one embodiment, the interface device further includes a rotatable section of a sample arm of an interferometer aligned with the aperture.

In one aspect, the invention relates to an interface unit. The interface unit includes a catheter connector configured to receive a disposable imaging probe comprising a rotatable optical fiber segment configured to transmit light, and a catheter body; a stationary optical fiber segment configured to transmit the light; an optical rotary joint comprising an optical coupler configured to couple the stationary optical fiber segment to the rotatable optical fiber segment; and an electrical rotary joint which includes a first annular ring defining a first annular opening and comprising a first conductive winding and a second annular ring defining a second annular opening and comprising a second conductive winding, wherein a first gap is defined between the first conductive winding and the second conductive winding and an elongate cavity is defined by the first and second annular openings, wherein the optical rotary joint and the electrical rotary joint are substantially coaxial and the light passes through the elongate cavity.

In one embodiment, the interface unit includes a stator defining a stator bore; and a rotor defining a rotor bore, wherein the stationary optical fiber segment is concentrically disposed in the stator bore. In one embodiment, the optical coupler is disposed within the elongate cavity. In one embodiment, the first conductive winding is disposed in a first ferrite ring and the second conductive winding is disposed in a second ferrite ring, wherein the ferrite rings are substantially parallel. In one embodiment, the rotor is at least partially disposed in the stator bore. In one embodiment, the stator is at least partially disposed in the rotor bore. In one embodiment, the first gap ranges from about 20 microns to about 100 microns.

In one embodiment, the second rotatable optical fiber segment and the fiber optic rotary joint are at least partially disposed in the elongate cavity and one or more of the conductive windings are annularly disposed around the fiber optic rotary joint. In one embodiment, the first conductive windings are stationary windings and the stationary optical fiber and stationary windings are connected to the stator. In one embodiment, the second conductive windings are rotatable windings and the rotary optical fiber segment and rotatable windings are connected to the rotor. In one embodiment, stationary windings and the stationary optical fiber are connected to the stator. In one embodiment, the rotary rotatable windings and the rotary optical fiber segment are connected to the rotor. In one embodiment, a ratio of a number of turns in the first conductive winding to a number of turns in the second conductive winding ranges from about 0.25 to about 4. In one embodiment, the ratio is specified to adjust for impedance mismatch or increase the signal return voltage. In one embodiment, a center tap connection is made between the stationary windings to reduce common mode noise. In one embodiment the stator comprises an outer surface wherein the outer surface extends to cover the first gap. In one embodiment a portion of the outer surface comprises an EMI shielding material.

In one embodiment, the interface unit includes a center tap connection with one or more stationary windings configured to reduce common mode noise. In one embodiment, the stator includes an outer surface wherein the outer surface extends to cover the first gap. In one embodiment, a portion of the outer surface comprises an EMI shielding material. In one embodiment, the interface unit a motor configured to rotate the rotatable optical fiber segment. In one embodiment, the catheter connector comprises a rotatable electrical wire. In one embodiment, the interface unit includes a connector hub configured to rotationally balance one or more rotatable components of the interface unit.

In one embodiment, the optical rotary joint and the electrical rotary joint are arranged along a common axis of rotation. In one embodiment, the interface unit includes a substantially cylindrical tube comprising a cylindrical surface defining an elongate channel configured to receive the rotatable electrical wire or a conductor in electrical communication with the electrical rotatable wire. In one embodiment, the first conductive winding is rotatable and the second conductive winding is stationary.

In one aspect, the invention relates to an interface unit. The interface unit includes a catheter connector configured to receive a disposable imaging probe comprising a rotatable optical fiber segment configured to transmit light along an optical path, a rotatable acoustic signal conductor, and a catheter body; a stationary optical fiber segment configured to transmit the light and define the optical path; an optical coupler configured to couple the stationary optical fiber segment to the rotatable optical fiber segment, wherein a first gap is defined between the rotatable optical fiber segment and the stationary optical fiber segment; and an electrical rotary joint comprising a first conductive winding and a second conductive winding, wherein a second gap is defined between the first conductive winding and the second conductive winding, wherein the rotatable acoustic signal conductor is in electrical communication with the first conductive winding; an elongate cavity defined between the first conductive winding and the second conductive winding; wherein the optical coupler and the electrical rotary joint are substantially coaxial and wherein the optical path spans the elongate cavity and the first gap.

In one embodiment, the first conductive winding is disposed in a first ferrite ring and the second conductive winding is disposed in a second ferrite ring, wherein the ferrite rings are substantially parallel. In one embodiment, the optical coupler, the electrical rotary joint and the rotatable acoustic signal conductor are arranged to rotate about an axis of rotation. In one embodiment, the optical path further spans the second gap. In one embodiment, the optical path is a section of a sample arm of an interferometer.

In one embodiment, the invention relates to an interface device. The interface device includes a cover; an aperture defined by the cover; a stationary section of a sample arm of an interferometer disposed within the cover and comprising a stationary optical fiber section having an endface; a first rotatable connector defining a first bore, the first bore positioned in alignment relative to the aperture and disposed within the cover; a sacrificial connector; a second rotatable connector defining a second hole, the first second positioned in alignment relative to the aperture, wherein the first rotatable connector and the second rotatable connector sandwich the sacrificial connector and; a first motor disposed within the cover, the first motor configure to rotate the second rotatable connector.

In one embodiment, the first rotatable connector comprises a first assembly and a second assembly, wherein the first assembly comprises an electrical contact, wherein the second assembly comprises a counterbalance. In one embodiment, the interface device includes an electrical signal coupling subsystem comprising a rotatable transformer component and a stationary transformer component. In one embodiment, the interface device includes an optical signal coupling subsystem comprising a rotatable optical component and a stationary optical component. In one embodiment, the interface device includes an optical connector disposed within the rotatable optical connector. In one embodiment, the interface device includes an elongate probe connector comprising one or more posts extending therefrom. In one embodiment, the interface device includes a rotatable section of a sample arm of an interferometer wherein the rotatable section is aligned with the aperture.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

In part, the invention relates to an interface unit such as a patient interface unit (PIU) configured for use with data collection probes having an optical data collection component and an ultrasound data collection component. The data collection components are configured to be introduced into a patient such as through a blood vessel and rotate therein in one embodiment. The PIU and a disposable data collection probe are configured to connect to and release from each other. In addition, one or more components of the PIU are configured to rotate in a synchronized manner with one or more components of the data collection probe. The data collection probe can include a catheter or one or more sheaths. The probe can further include imaging devices and optical and electrical components such that both IVUS and OCT data can be collected.

While PIUs are currently in use for a single type of imaging such as a PIU for IVUS or a PIU for OCT, each of these types of PIU cannot be used with other type of imaging system. Thus, an OCT PIU does not work with an IVUS PIU and vice versa. A multimodal or combination PIU that can work with an IVUS system, an OCT system, and a combination IVUS and OCT system faces numerous design challenges that result from combining and arranging optical and acoustical components along with the necessary mechanical and electrical subsystems. In part, one embodiment of the invention addresses such challenges by including one or more of a rotary joint such as a combination rotary joint, a catheter body such as a combination catheter body, a pullback section, a connector such as a combination connector, and electromagnetic interference or electromagnetic interference (EMI) reduction components.

In one embodiment, the use of the term combined or combination refers to the relevant combined or combination apparatus or method steps having characteristics, properties, components, or other features relating to combining or otherwise supporting the use of a first imaging mode or modality such as an optical imaging technology and a second imaging mode or modality such as an acoustic imaging technology. OCT and IVUS are non-limiting examples of two such imaging technologies.

Figure 1:
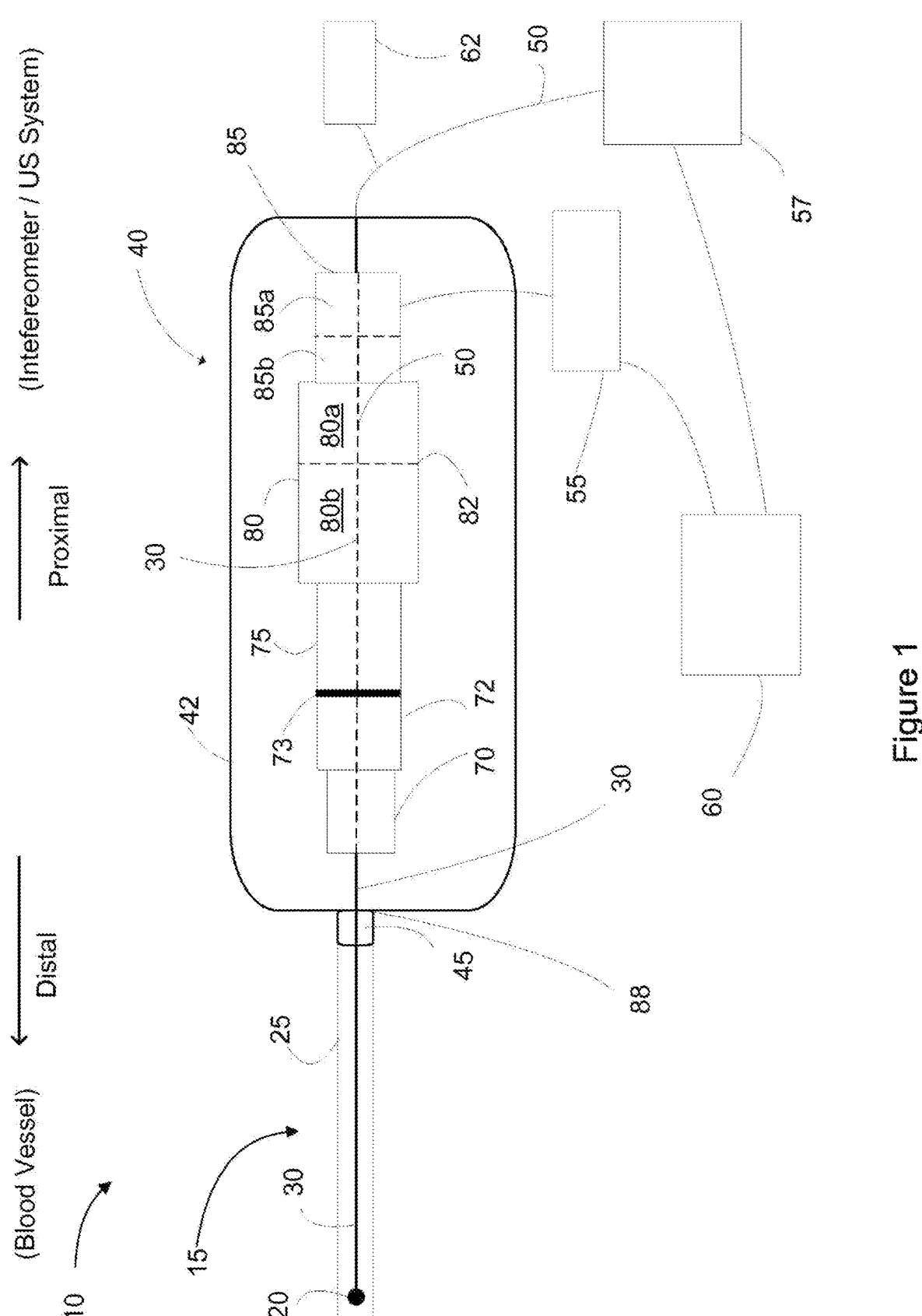
FIG. 1 is a schematic diagram of an image data collection system that includes a PIU in accordance with an illustrative embodiment of the invention.

FIG. 1 illustrates a data collection system 10. The system 10 includes a data collection probe 15. The probe 15 includes a probe tip 20. The probe tip 20 is disposed in a sheath 25. The sheath is sized for insertion into a sample such as a blood vessel. The probe tip 20 is in optical communication with an optical fiber 30. The system 10 also includes a PIU 40. The PIU 40 includes an outer cover 42 with regions for one or more control elements such as buttons or switches. The PIU 40 includes a probe connector 45. In one embodiment, the probe connector 45 is configured to slide inside the PIU 40. The probe 15 is configured to connect to the PIU 40 via probe connector 45. The probe tip can include a beam director and/or an ultrasound transducer. The sheath 25 can include a region such as a window through which optical and acoustic image data can be collected. In one embodiment, the probe 15 is terminated with a dual purpose optical/electrical probe connector or terminal connector 45 which connects with the PIU 40. The probe connector 45 rotates with and is connected to the probe 15.

The PIU 40 is configured to receive an optical signal from a beam director and an electrical signal from an ultrasound transducer in the data collection probe 15 while the data collection probe spins. In addition, the PIU is configured to transmit the optical signal along an optical path that includes a rotatable fiber section 30 that is in optical communication with one or more stationary optical fiber sections 50 and a stationary optical receiver 57 such as one or more photodiodes. The optical path along which the optical signal travels to and from a sample constitutes the sample arm of an interferometer in one embodiment. As a result, the sample arm of the interferometer spans one or more components in the PIU 40 in one embodiment. The sample arm includes one or more lengths of optical fiber in one embodiment.

Similarly, the PIU 40 is configured to transmit an ultrasound (US) signal along an electrical path that includes one or more conductors and other circuit elements such as a transformer that is in electrical communication with an ultrasound signal system 55. The ultrasound signal system 55 can include a receiver for receiving the ultrasound signal and a controller for driving the ultrasound sound transducer in the probe 15. As a result, some components of the PIU are rotatable and configured to rotate with the data collection probe in a rotationally balanced and/or synchronized manner while other components of the PIU such as optical fiber section 50 are stationary.

The optical and US signals are transmitted to data processing system 60 as electrical signals in one embodiment. The data processing system 60 includes memory storage and one or more processors suitable for transforming the optical and US signals into cross-sectional images, longitudinal images, or other images of the blood vessel which was imaged during a pullback procedure using probe 15. An optical source 62 such as a laser can also be in optical communication with the probe 15 via the PIU 40. A reference arm of an interferometer that terminates at a movable reflector can also be part of the system that optically or electrically connects to the PIU.

As shown in FIG. 1, the PIU 40 includes various components that are supported by a frame, carriage, and/or other structural members disposed within the cover 42. A connector 70 is shown within the PIU 40. One end of connector 70 faces an aperture 88 of the PIU 40. In one embodiment, the probe connector 45 can slide within the PIU via aperture 88 which is defined by a region of the cover 42. In one embodiment, the connector 70 includes two sections that snap or otherwise connect together. The connector 70 includes a channel configured to receive an optical fiber from the probe 15 and one or more electrical contacts configured to form an electrical connection with the probe 15. The connector 70 is configured to rotate relative to an axis of rotation that is aligned with optical fiber disposed in connector 70.

Still referring to FIG. 1, a PIU connector 72 is in series with connector 70. A sacrificial joint 73 can be used to connect PIU connector 72 and connector 70 such that these two connectors 70, 72 can be connected and released from the sacrificial joint 73 to facilitate PIU maintenance and repair. A motor 75 such as a belt driven motor can be used in one embodiment to rotate or pullback probe 15. The PIU 40 can also include an optical coupling device or joint 80 such as fiber optic rotary joint. The optical joint 80 includes a stationary component 80a and a rotatable component 80b. The optical fiber section 30 is in optical communication with the data collection probe and rotates with the probe. In turn, the optical fiber section 50 does not rotate and is in optical communication with an optical signal receiver 57.

Each of these two optical fiber sections 50, 30 are arranged at such that their respective endfaces are aligned in optical joint 80 such that light can travel between the stationary fiber section 50 and rotatable fiber section 30. In one embodiment, an air gap is disposed been the end faces of fiber sections 30, 50 such that light can jump through the air gap and travel from one fiber section 30 to fiber section 50 and vice versa.

The optical joint 80 is configured such that the optical signal containing depth information obtained during a scan of a blood vessel can be coupled from a rotating fiber and used by a stationary system. Similarly, the electrical ultrasound signals are similarly coupled using an electrical signal coupler or joint 85 configured to transmit signals from a rotating electrical connection to a stationary electrical receiver. The electrical signal coupler or joint 85 is configured to operate in a contactless manner such that the electrical signal containing ultrasound depth information or other ultrasound data is transmitting using induction, wireless or other components. The electrical signal coupler or electrical rotary joint 85 can include a stationary component 85a and a rotatable component 85b.

In one embodiment, the electrical signal coupler includes a first and second transformer portion such as a first ferrite device and a second ferrite device. The transformer portions such as the ferrite devices are disk or ring shaped in one embodiment. In one embodiment, the electrical signal coupler includes a center tap to the transformer such that the IVUS signal is transmitted between the two ends wires of the transformer and a common mode signal is received at the center tap. Additional details relating to an exemplary PIU are discussed below with respect to FIG. 2 and as otherwise provided herein.

Figure 2:
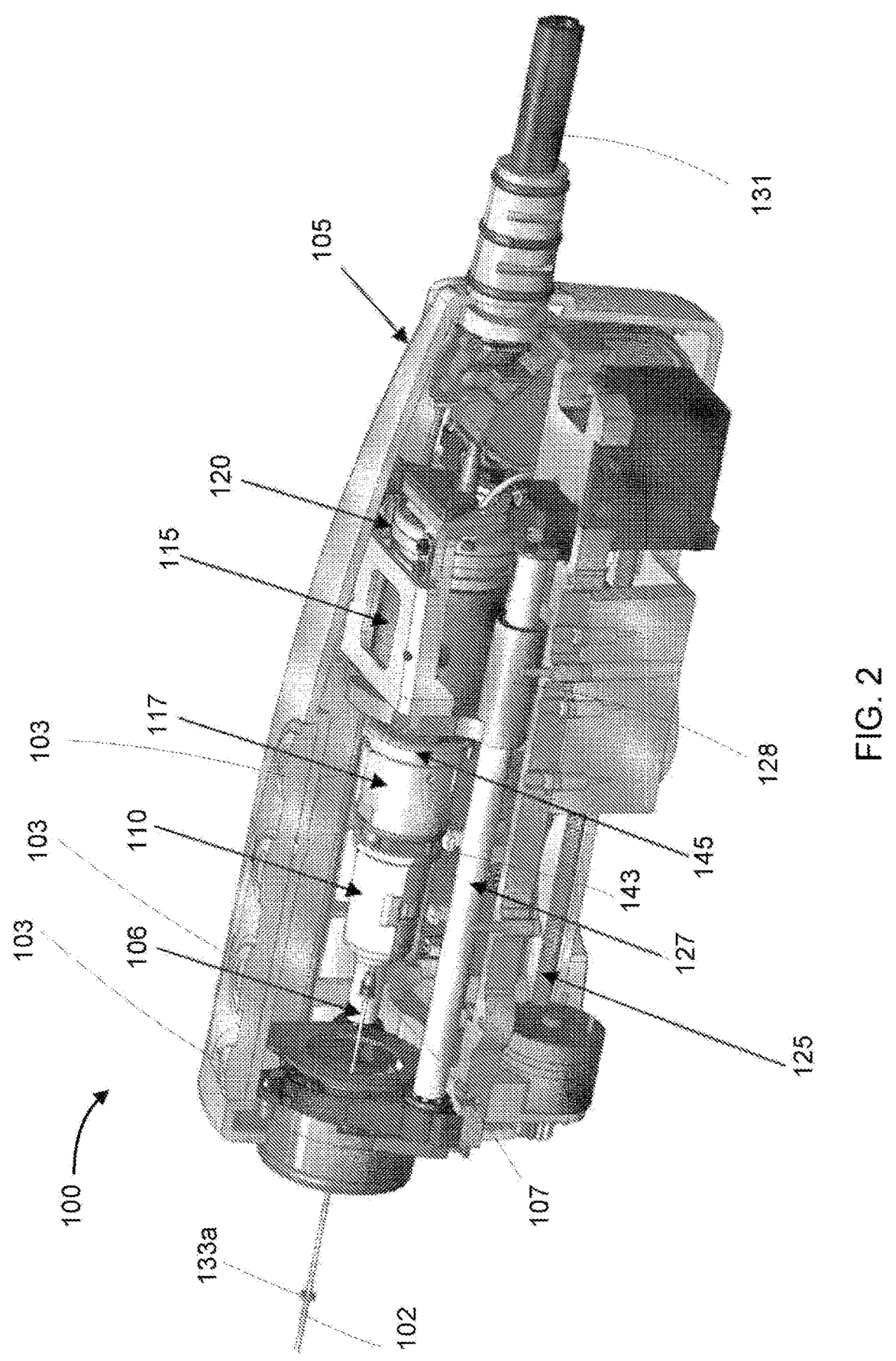
FIG. 2 is a perspective diagram of a patient interface unit (PIU) in accordance with an illustrative embodiment of the invention with part of its cover removed.

FIG. 2 shows a side perspective view of an exemplary PIU 100 that is connected to a disposable data collection probe that includes an imaging core 102. The imaging core 102 includes an optical fiber. The imaging core can include other coatings or materials disposed or wound relative to the optical fiber. The optical fiber defines an optical path which is a portion of a sample arm of an interferometer.

The PIU 100 can include one or more actuatable controls 103 such as switches or buttons. Portions of the PIU cover 105 are shown with respect to various components of the PIU 100. In one embodiment, the controls 103 are positioned relative to holes defined by the PIU cover 105. The imaging core 102 is connected to a probe connector 107. This connector 107 can be an elongate member having a cylindrical, conical, partial conical or other geometry. The connector 107 can include posts around which wires can be wrapped and adhered. In one embodiment, this probe connector 107 is a dual optical and electrical connector that is connected to the end of a data collection probe via the imaging core 102.

The PIU 100 is configured to rotate a probe while an optical fiber in the probe transports light along an optical path for the OCT data collection. In addition, the PIU 100 is configured to transmit one or more electrical control signals suitable for controlling or driving an ultrasound transducer such that acoustic beam formation occurs. The electrical path for controlling the transducer is also used for transmitting signals containing ultrasound data obtained with respect to the blood vessel being scanned with a data collection probe. Similarly, the PIU 100 is configured to cause the probe which includes imaging core 102 to be withdrawn from the vessel at a constant rate as the image is being acquired during a pullback.

Referring again to FIG. 2, the PIU 100 is configured to optically couple and electrical couple with a data collection probe having a probe tip and the optical and acoustic data collection elements described herein. Specifically, the PIU is configured to couple with the rotating optical fiber and the rotating conductors using a stationary optical fiber section disposed in the PIU and electrical conductors disposed in the PIU 100. The PIU 100 includes a probe connector 110, a PIU interconnect 117 that includes a sacrificial joint, and a fiber optic rotary joint 115 to perform the optical coupling and a rotary transformer 120 to perform the electrical coupling, respectively.

An electrical connector that plugs into sacrificial interconnect of PIU interconnect 117 is disposed inside connector 110. In one embodiment, the sacrificial interconnect of PIU interconnect 117 and probe connector 110 are configured such that as they engage or push against each other an electrical connection and optical connection form such that optical signals and electrical signals from the probe tip can pass through these two components. During pullback, the imaging core 102, the catheter connector 110, the PIU connector 117 with sacrificial interconnect 143, the fiber optic joint 115 and the rotary electrical joint 120 all slide back together along the bushing rails 127. The sacrificial joint 143 can also be referred to as a sacrificial interconnect or sacrificial connector in one embodiment.

In one embodiment, the probe connector 110 is formed from two shells or halves that snap or otherwise connect together. In order to balance the probe connector 110, and the sacrificial and other connectors of PIU interconnect 117, in one embodiment to the extent an electrical, optical or other element is disposed on one side of the interior of the probe connector 110 or PIU interconnect 117, a counterbalance is disposed on the other side in the interior of probe connector 110 or PIU interconnect 117.

In one embodiment, the counterbalance reduces wear, wobble, and other unwanted effects during rotation of these components of the PIU 100. Specifically, it is advantageous to reduce the rotational imbalance or dynamic forces placed on the probe, connector and rotating portions of the PIU. The electrical component in the probe connector 110 can be counter balanced using a dummy circuit having a similar shape and mass or substantially the same shape and mass as the electrical component.

In one embodiment, the PIU interconnect 117 of the PIU 100 includes a double ended optical connector and electrical connector. This sacrificial connector is configured such that a worn connector port can be replaced without rewiring the electrical contacts or replacing the long optical fiber that connects to a data processing system.

Still referring to FIG. 2, an optical rotary joint 115 is positioned in series with a PIU interconnect 117. The optical rotary joint 115 includes an optical stationary joint component and an optical rotatable joint component in one embodiment. The electrical rotary joint 120 includes an electrical stationary joint component and an electrical rotatable joint component in one embodiment. The rotatable joint component is configured to spin or rotate relative one or more axis. In one embodiment, the optical stationary joint component and the electrical stationary joint component are arranged in series with each other. In one embodiment, the optical rotatable joint component and the electrical rotatable joint component are arranged in series with each other.

The PIU 100 also includes a rotary transformer 120. The transformer 120 can be a center tap transformer in one embodiment. One or more wires in electrical communication with transformer 120 provide an electrical path for the ultrasound data signal generated using a data collection probe to be transmitted to an ultrasound receiver. The transformer 120 is configured such that the ultrasound signal is received from the probe in a contactless manner using a changing electric or magnetic field. In one embodiment, the transformer 120 includes a stationary ferrite ring and a rotating ferrite ring. A gap is disposed between the rings. As the probe rotates, conductors in the probe carrying the ultrasound signal spin. These spinning or rotating conductors terminate near a rotatable section of the transformer 120. The transformer 120 includes a rotating assembly and a stationary assembly in one embodiment.

In one embodiment, the rotatable portion of the transformer and the rotatable conductors in the probe are synchronized to rotate together. The stationary portion of the transformer 120 receives electrical signals by induction or another field-based effect from the rotating portion of the transformer. In one embodiment, each of the stationary portion of the transformer 120 and the rotatable portion of the transformer 120 has a plurality of windings. The windings are the same for both the stationary and rotatable portions of the transformer in one embodiment.

In one embodiment, the rotatable parts in the PIU 100 and the probe connector 110 are designed to be rotationally balanced. Thus, in one embodiment, the PIU 100 includes a serial arrangement of a plurality of elements configured to receive an optical fiber and reduce rotational inertia when coupled to a data collection probe. The data collection probe includes a torque wire and a probe tip in one embodiment.

In order to acquire images at rapid image data acquisition speeds, a motor (not shown) rotates the imaging core 102, connector 110, PIU interconnect 117, a portion of the transformer 120 and a portion of the fiber optic rotary joint 115. The frequency of rotation ranges from about 100 Hz to about 250 Hz. Rotation at these speeds will cause significant vibration and noise unless the system is rotationally balanced. The system is configured such that when the system is rotating the probe body is balanced such that wobble and other vibrations are reduced. The use of counterbalances in the connector 110, and the sacrificial connector 143 provide rotational balance.

Further, a rapid pullback speed is also a feature the PIU. In part, pullback is achieved using a pullback motor (not shown) and lead screw 125 to slide a carriage 128 supporting the rotary transformer and the fiber optic rotary joint along bushing rails 127 at speeds that range from about 18 to about 50 mm/sec.

In FIG. 2, a bushing 133*a* is a shown. In one embodiment, a bushing and a distal seal (not shown) can be used. The seal can be positioned relative to other connecting elements such as an outer connector shell to prevent saline from entering the PIU when saline is used to purge a catheter used with the data collection probe. The stationary optical and electrical signals can be transmitted from the PIU through a jacketed conduit 131.

Figure 3A:
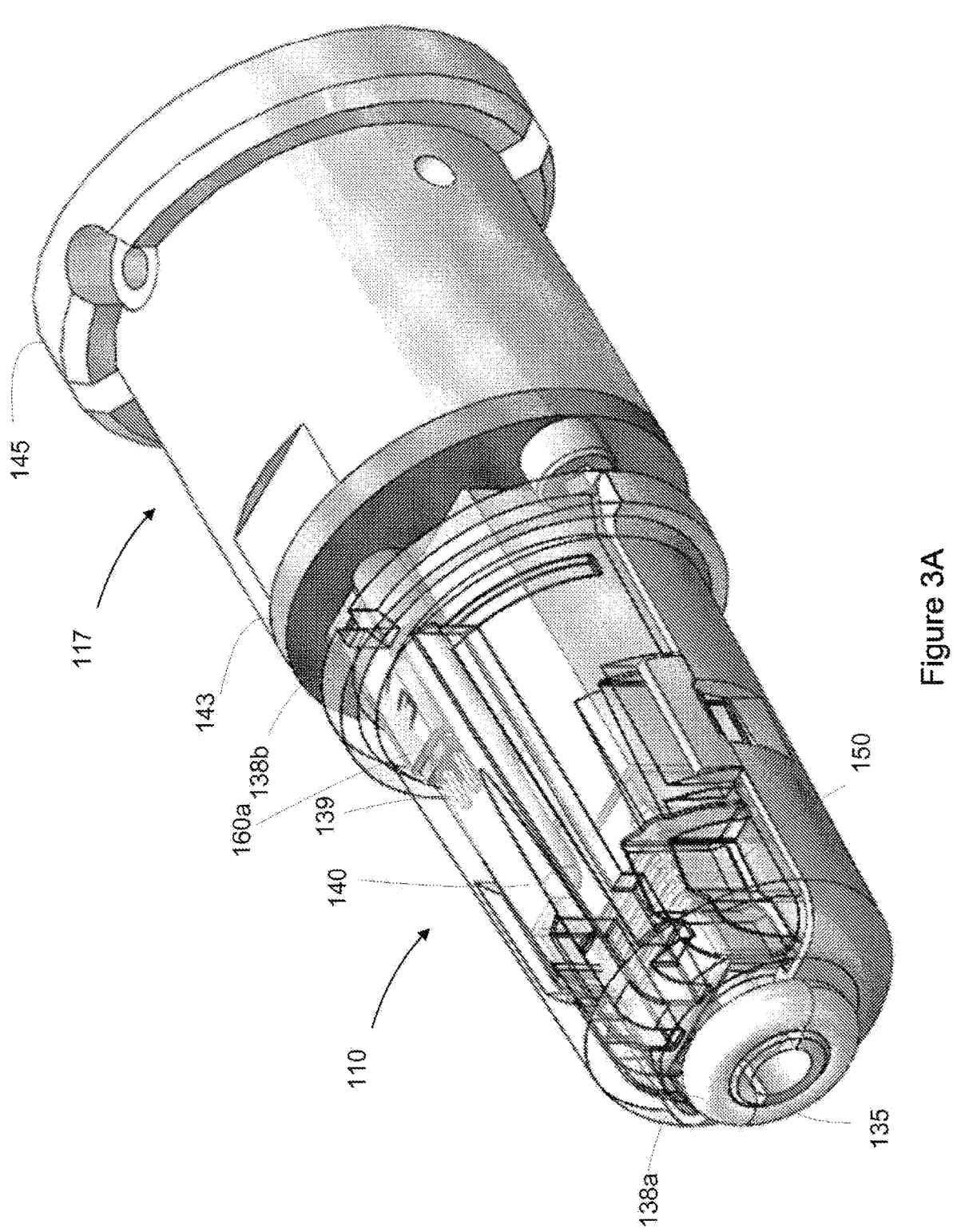
FIGS. 3A-3D are perspective views of components of a PIU including a sacrificial joint in accordance with an illustrative embodiment of the invention.

FIG. 3A is a perspective view of an exemplary probe connector 110 such as shown in FIG. 2. This probe connector 110 spins or rotates within the PIU 100. In one embodiment, the probe connector 110 includes a first section or shell and a second section or shell that snap or otherwise connect together to form the connector 110. For the purposes of illustrating features of the embodiment shown in FIG. 3A, the top half of the inner shell on the probe connector 110 has been made translucent to show the inside. The transparent top portion is an example of one such shell or section.

In one embodiment, the probe connector 110 includes an aperture 135 that is defined by a probe facing end face 138*a*. The probe connector continues from the endface 138*a* along an outer surface that terminates at second endface 138*b*. The first and second endfaces are both circular in one embodiment with different diameters as shown. The connector is cylindrical or bell shaped in one embodiment. A PIU interconnect 117 is shown in 3A. In addition, an electrical connector 139 and an alignment pin 140 are now made visible.

The PIU can include a sacrificial joint 143 in one embodiment. This joint 143 is sandwiched between and connects probe connector 110 and the PIU interconnect 117 in one embodiment. The inner shell of probe connector 110 has a male/male electrical connector 139 (left side is soldered to probe conductive wires in one embodiment) as well as one optical connector 150 attached or otherwise optically coupled to an optical fiber of the imaging core 102. The sacrificial joint 143 has a female (shown) 160*a* and male (not shown electrical connector as well as both sides of the optical connector (only one side shown). This entire sacrificial joint 143 can be replaced when it is worn without taking the entire PIU apart.

Figure 3B:
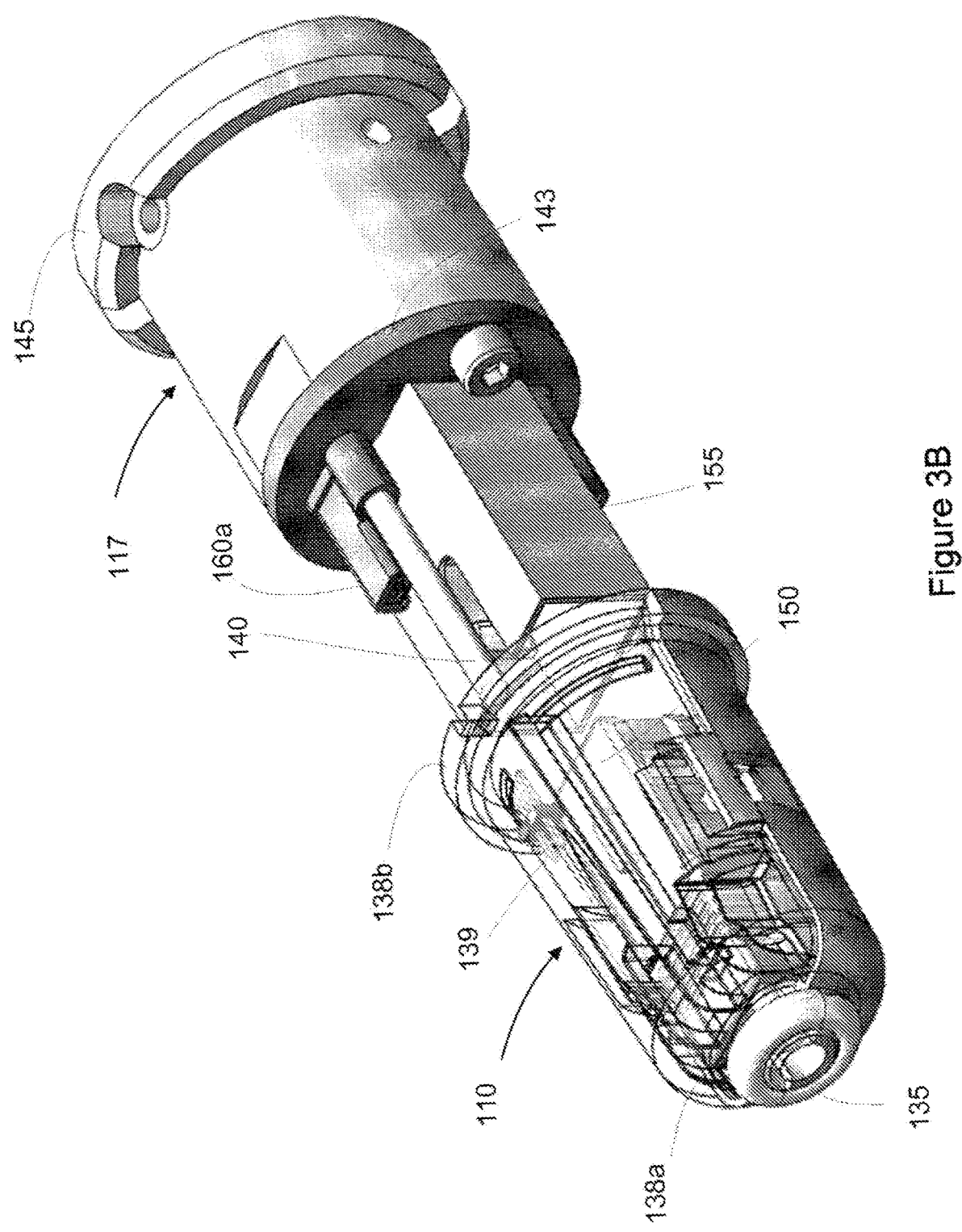

In FIG. 3B, the inner shells and the sacrificial interconnect 143 are depicted in an exploded view. Sacrificial interconnect 143 includes a female optical connector 155 shaped to receive the male optical connector 150. The cross-section of the female optical connector 155 is shown as rectangular in this embodiment. The endface or connector 145 of the PIU interconnect 117 is also shown. The endface 145 has a circular shape with a diameter. The diameter of endface 145 is greater than the diameter of endface 138*b* which is in turn greater than the diameter of endface 138*a* in one embodiment.

Figure 3C:
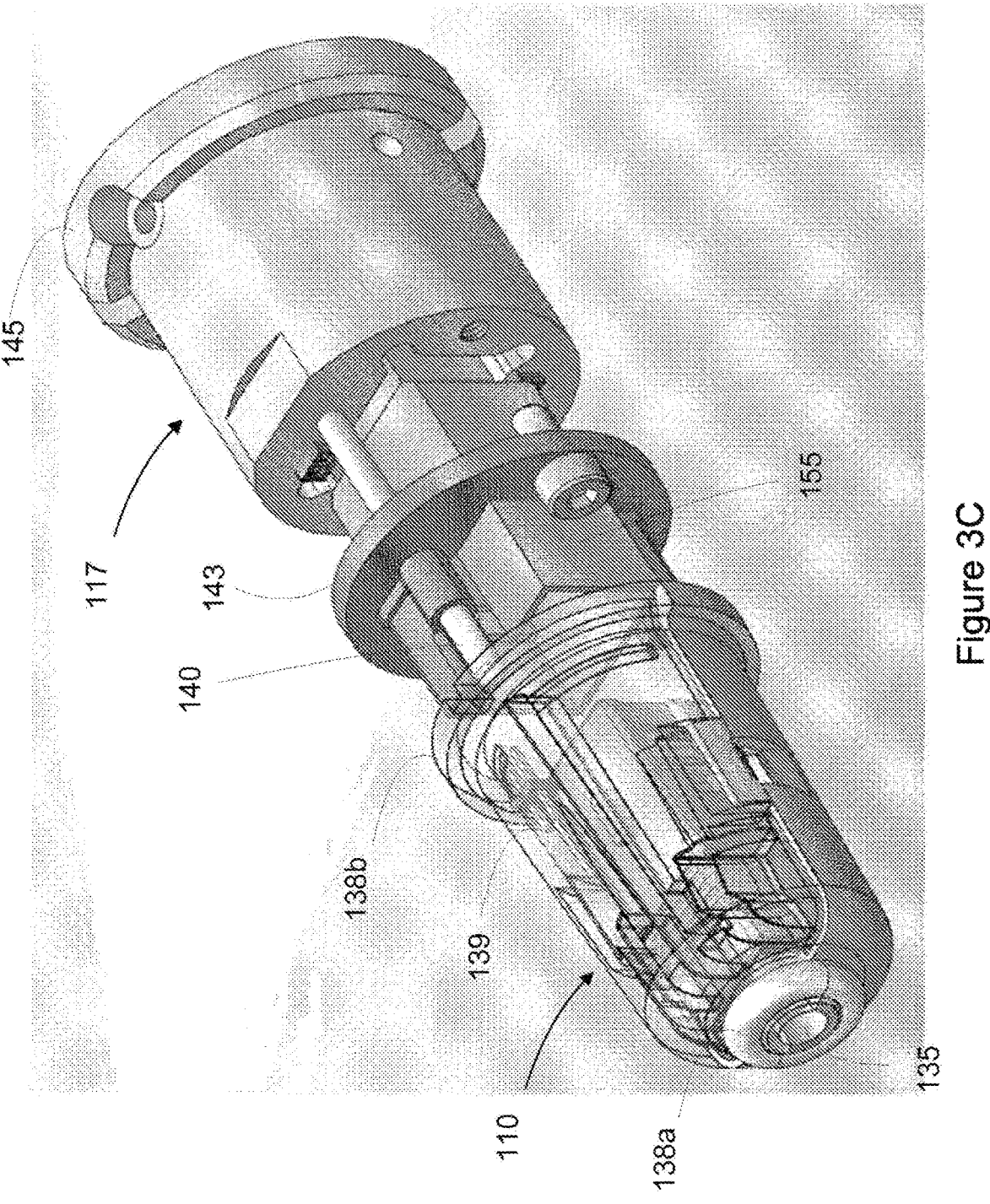
Figure 3D:
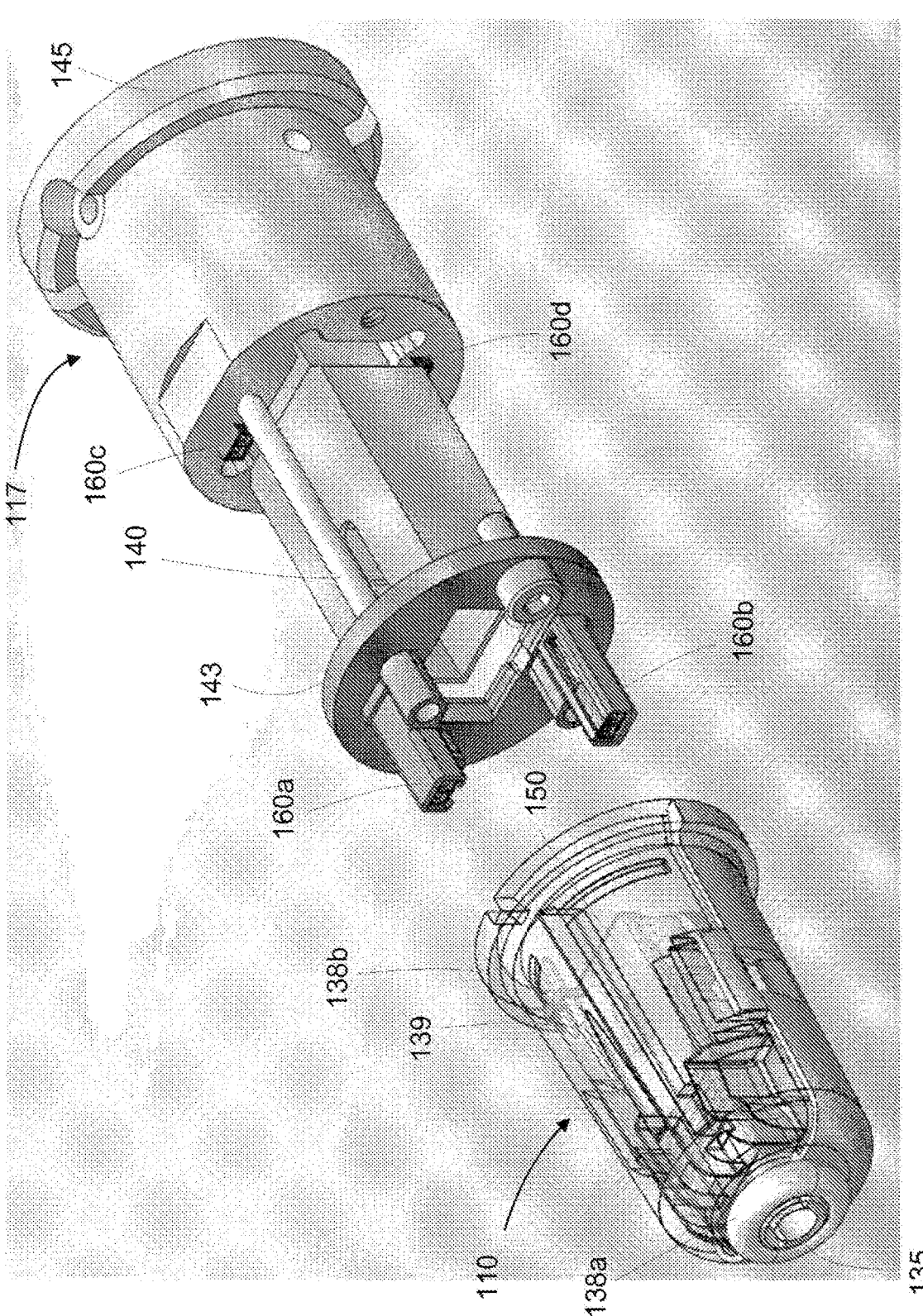

FIG. 3C shows another exploded view of components of the PIU with the sacrificial joint shown at a further separation distance from connector 110. In FIG. 3D, another exploded view is provided with the probe connector 110 withdrawn from the sacrificial joint. The sacrificial interconnect includes double ended electrical connectors 160*a* and 160*b*. Connectors 160*c* and 160*d* are single ended electrical connectors. A pair of "dummy connectors" 160*b* and 160*d* in both the sacrificial joint and the PIU connector 145 are shown.

In one embodiment, these connectors 160*a* and 160*b* and 160*c* and 160*d*, respectively, are configured to match or substantially match as pairs in the probe connector 110 and the PIU connector 145, respectively, in terms of mass and relative to position such that they counterbalance each other. This contributes to the rotational balances of elements in the PIU. In one embodiment, the PIU includes a counterbalance configured to maintain rotational balance in a PIU component such as an electrical or other component on one side of a rotatable connector. The counterbalance is arranged in a symmetric manner relative to the operative connector element it is provided to balance relative to in a given PIU component.

Figure 4A:
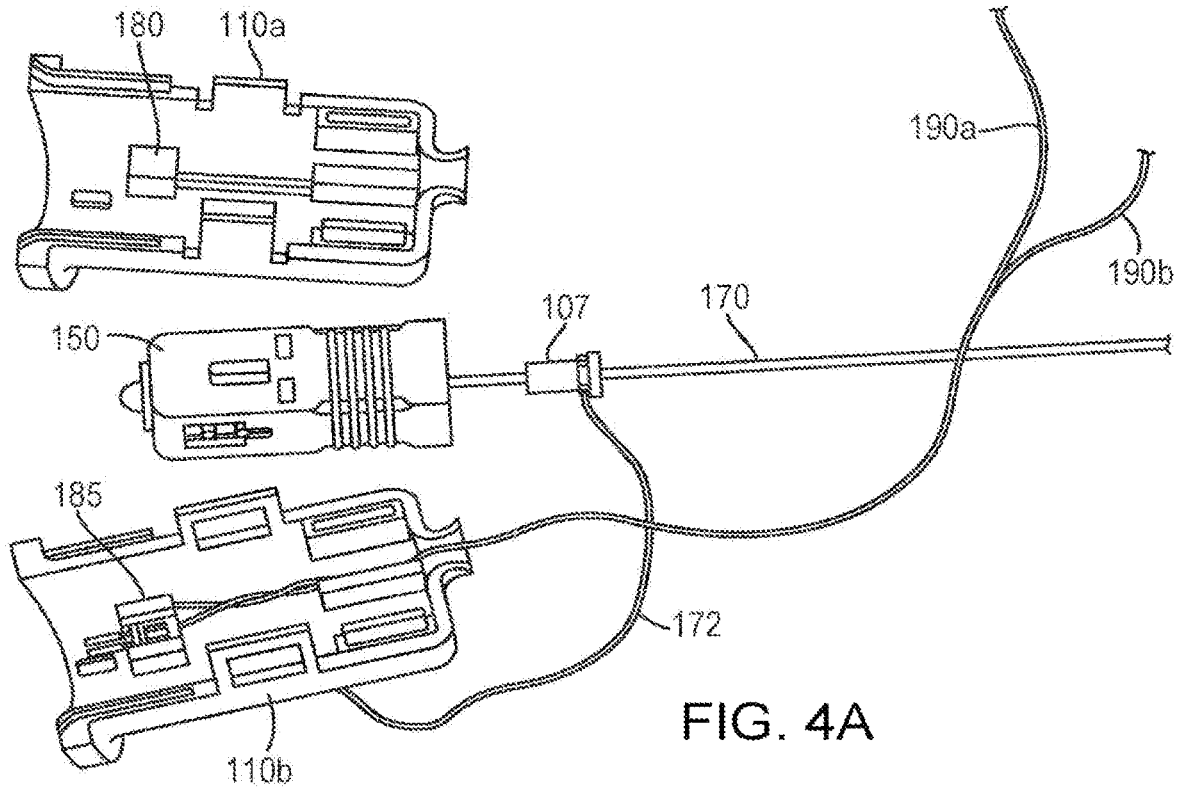
FIGS. 4A-4B show components of an optical connector and an electrical connector in accordance with an illustrative embodiment of the invention.

FIG. 4A depicts two sections 110*a*, 110*b* of the probe connector 110 shown as halves positioned to reveal the inner shell of connector 110. The two inner shell halves 110*a*, 110*b* are positioned on either side of an optical connector 150 mounted on the end to receive the optical fiber. One of the inner shell sections 110*b* is modified to include the electrical connector 185.

In one embodiment, the other inner shell section 110*a* has a counterbalance 180 symmetrically arranged on the other section 110*b* relative to wherein the connector 185 is positioned on section 110*a*. This counterbalance can be a blank or other weight. The counterbalance can be formed in the same material used to make connector 110. The counterbalance 180 balances the electrical connector 185 in section 110*b*. The optical connector 150 mounted on the tube 170 incorporates the optical fiber shown in FIG. 4. Additional electrical conductors such as wires 190*a*, 190*b* are shown in electrical communication with electrical connector 185 in FIG. 5B.

Figure 4B:
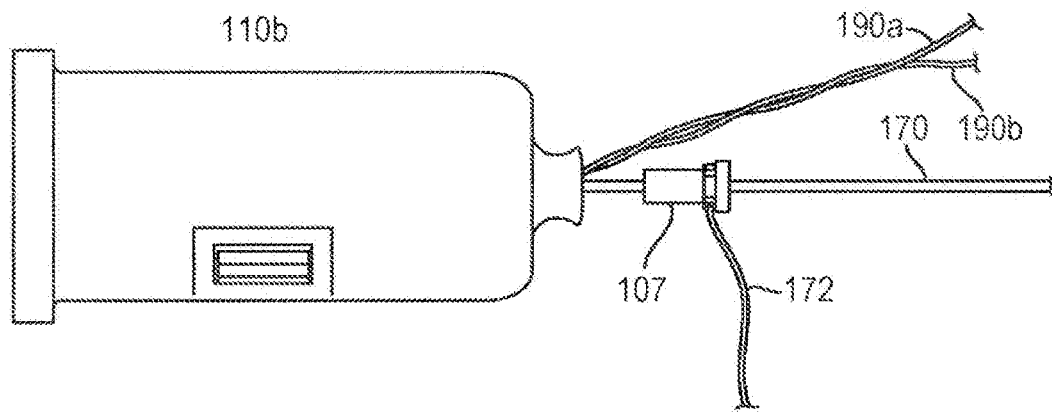

In FIG. 4B, the two inner shell halves are show together as connector 110. In one embodiment, the two inner shell halves are configured such that they can snap together around the optical connector 150. A plurality of electrical wires received from the electrical connector 185 exit the shell. Conductor 172 from the probe connector 107 is in electrical communication with electrical connector 185 in one embodiment. The electrical connector 185 transmits the ultrasound signal along an electrical path to rotary transformer 120. Electrical connector 185 rotates with the data collection probe when the PIU rotates the probe. In one embodiment, the elements disposed inside the inner shell will rotate at a frequency that ranges from about 100 to about 250 Hz.

Figures 5A, 5B:
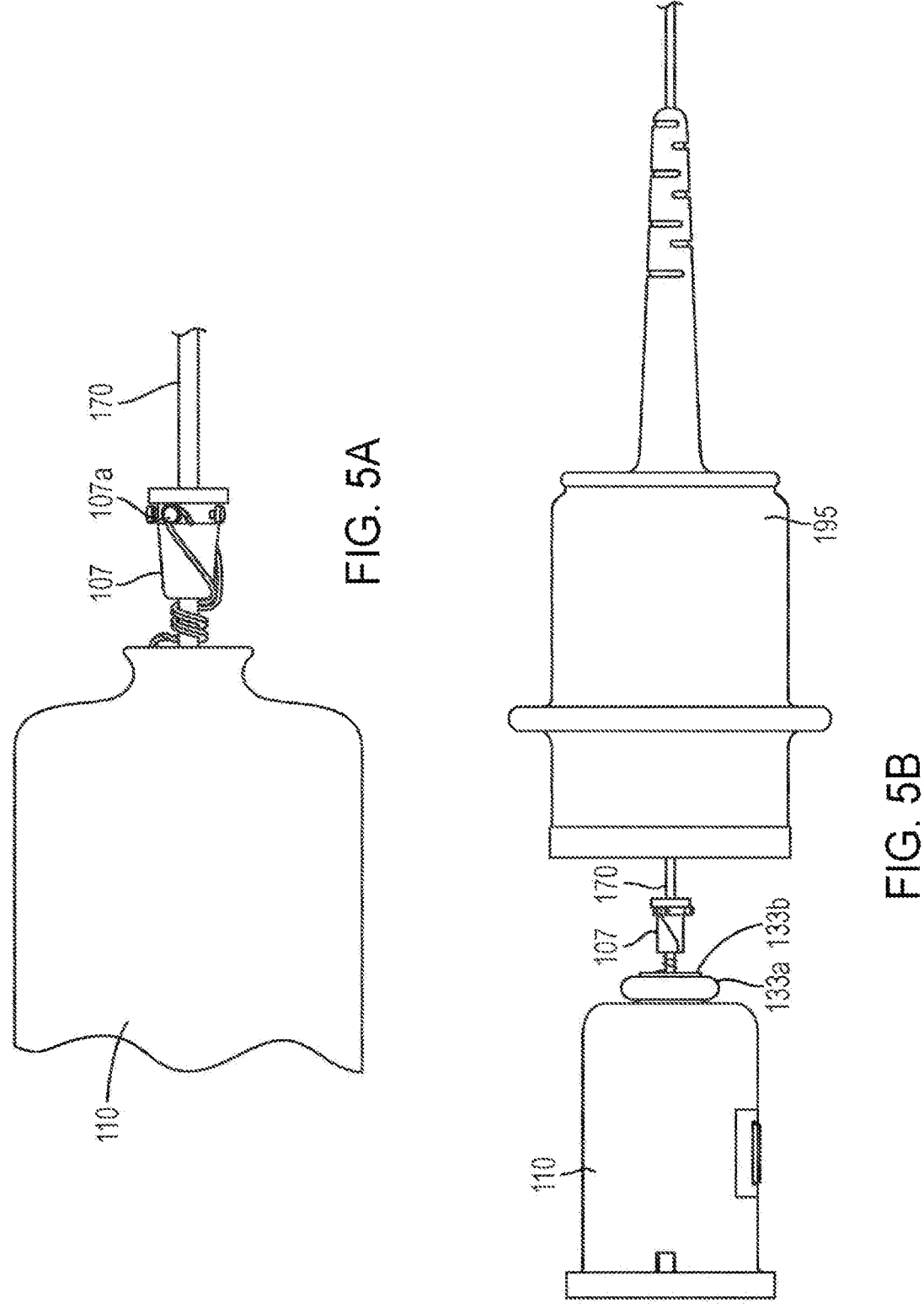
FIG. 5A shows electrical connections relative to a connector component of a PIU in accordance with an illustrative embodiment of the invention.
FIG. 5B shows rotatable connector and a fixed connector configured to receive the rotatable connector accordance with an illustrative embodiment of the invention.

FIG. 5A shows electrical wires exiting the shell. Wires 190a, 190b have now been soldered to the electrical wires 172 exiting the tube 170. As a result, an electrical path is defined from the probe connector 110 and PIU connector 117 along the length of the imaging probe. The wiring interconnect 107 includes one or more protrusions or posts 107a as shown. These posts 107a are formed or connected to the connector 107. The wires 190a, 190b from the probe connector 110 and the wires from the probe 172 can be wrapped around such posts 107a and soldered or otherwise secured. Any excess wire resulting after the wrapping and/or soldering can be cut such that the connection remains secure during rotation.

FIG. 5B shows probe connector 110 and a connector shell or connector cover 195 aligned relative to each other. The rotatable probe connector 110 nests inside of the fixed outer shell also referred to as a connector cover 195 or outer connector 195. The rotatable probe connector 110 and the stationary connector 195 slide relative to each other such that probe connector 110 moves inside and outside of connector 195. In one embodiment, during a pullback, probe connector 110 moves inside stationary connector 190. Probe connector 110 and stationary connector 190 are configured to prevent the backflow of any saline or other catheter purging fluid along with the bushing 133a, 133b or other fluid restricting components.

Rotary Joint Embodiment

One or more rotary joints are used to couple two rotating signal transmission lines (optical fiber and plurality of coiled conductors such as wires) within the probe to stationary transmission lines within the PIU. In one embodiment, each rotary joint is a contactless joint because it is configured to couple an optical signal over an air gap or an electrical signal over an air gap. A fiber optic rotary joint is configured such that the optical fiber portion of the joint is coaxial with the axis of rotation in one embodiment. This in turn requires the electrical rotary joint to have a central core which defines a cavity, channel or opening to allow passage of an optical fiber or otherwise define an optical path. Additionally, because both rotary joints have a rotating and stationary part, the central core is sized and otherwise configured to allow for various structural elements to link rotating and non-rotating elements.

Figure 6A:
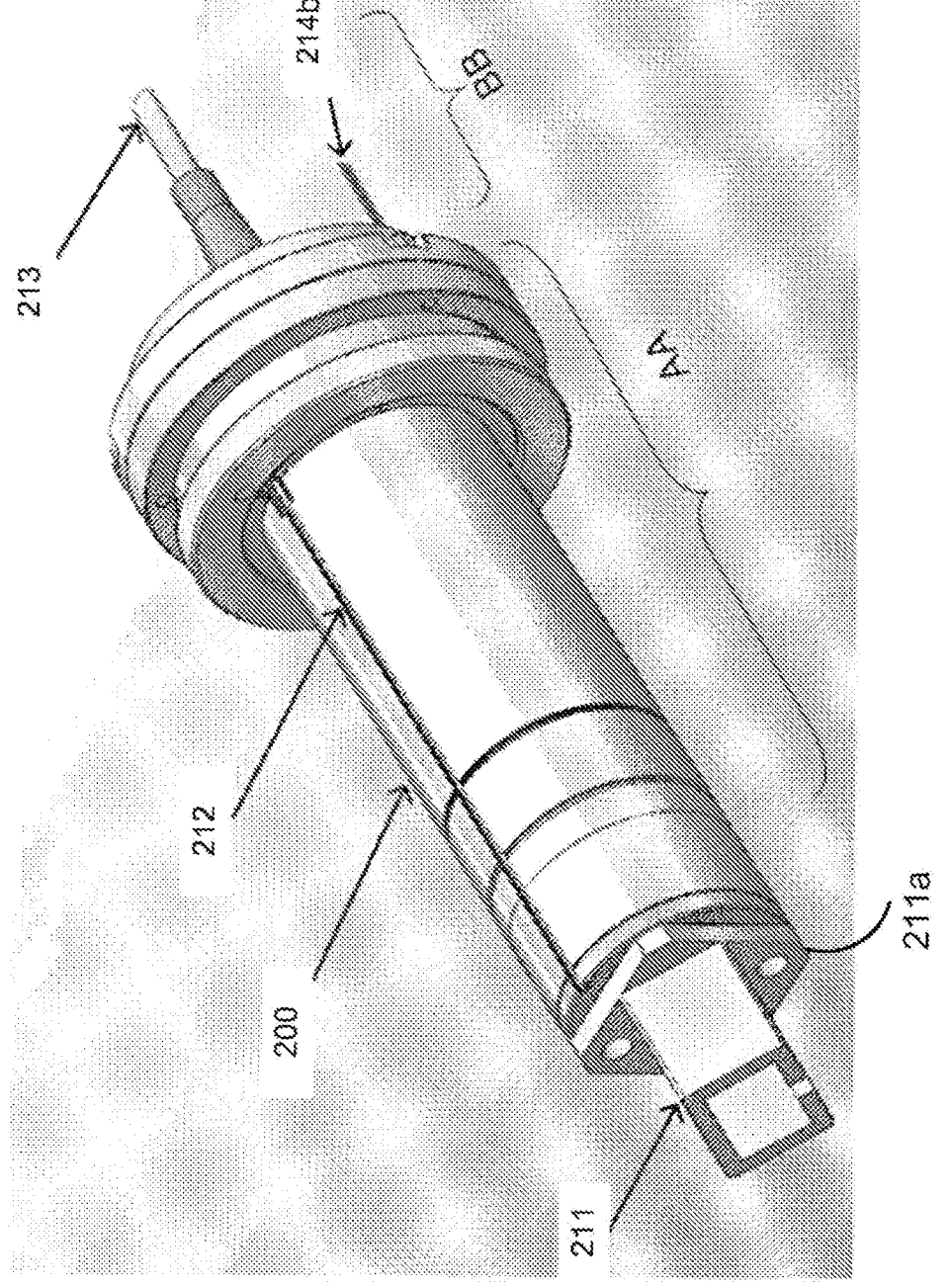
FIG. 6A is a perspective diagram of the outside of a combination rotary joint m accordance with an illustrative embodiment of the invention.

An embodiment of a combination rotary joint is shown in FIG. 6A. This embodiment of a combination rotary joint 200 has a rotatable end AA and a stationary end BB. The rotating end AA includes a rotating fiber connector 201 and a rotatable channel 212 to receive an electrical wire connecting to the rotatable electrical connector (not shown). In one embodiment, the electrical wire disposed in rotatable channel 212 is a rotatable acoustic signal conductor. Rotatable channel 212 is configured to allow a rotatable acoustic signal conductor such as a conductive wire to be recessed relative to a cylindrical pipe or shell of an exemplary rotary joint or component thereof. The conductor disposed in the channel 212 couples signals to and from an acoustic wave generator transducer in the probe tip. This coupling of acoustic signals occurs as the channel 212 rotates in one embodiment such as during a pullback of a combination OCT and IVUS probe.

Still referring to FIG. 6A, the stationary end BB has a stationary optical fiber 213 and a stationary electrical wire 214b. Optical signals collected using a data collection probe and light received from a light source are transmitted through the optical fiber 213 and an optical fiber (not shown) connected to the rotatable optical fiber connector 211. The rotatable optical fiber connector 211 of FIG. 6A is an exemplary embodiment of connector 45 shown in FIG. 1. The optical fiber connector 211 can include a support plate 211a as shown.

Figure 6B:
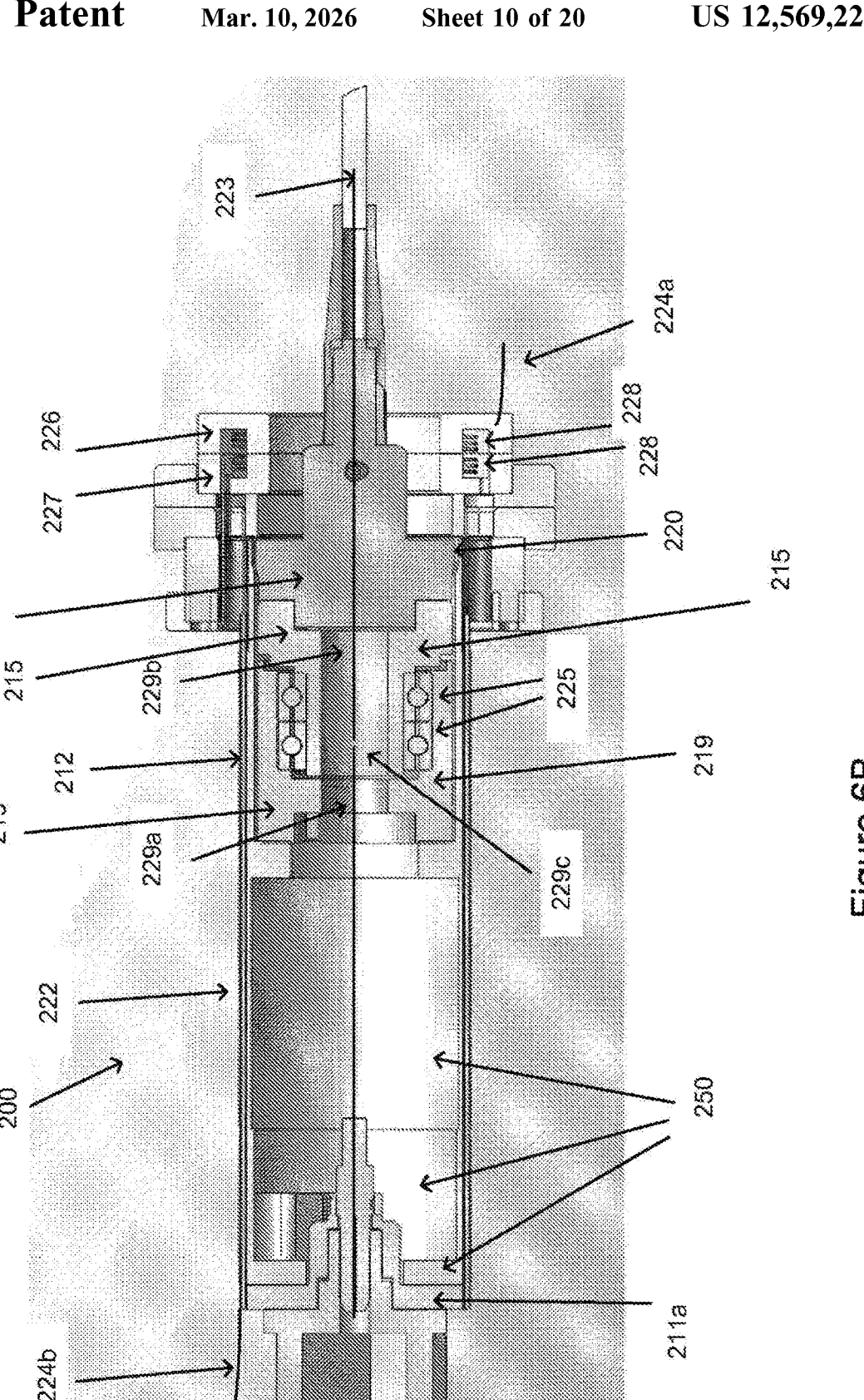
FIG. 6B is a cross-sectional diagram of the combination rotary joint of FIG. 6A.

A cross section of the combination rotary joint 200 showing the internal structure of the combination rotary joint of FIG. 6A is depicted in FIG. 6B. The electrical portion of the rotary joint 200 includes a first plurality of windings disposed adjacent to a second plurality of windings with a gap disposed there between such that one set of windings may rotate relative to the other. These windings constitute a transformer or a portion thereof. A set of facing annular ferrite rings 226 and 227; one rotatable 227 and one stationary 226 can be used to implement the windings as shown.

Specifically, each plurality of windings can be implemented using annular rings 226 and 227 are made of ferrite and each having a concentric circular coil 228 imbedded in the ferrite ring. The coil of the rotatable ring 227 is connected to the electrical wire 224b which connects to an rotatable electrical connector on a disposable data collection probe. For example, electrical wire 224b is in electrical communication with an ultrasound transducer, which is a component of an imaging probe tip. An exemplary probe tip 20 is shown in FIG. 1. With respect to FIG. 6B, the coil of the stationary ring 226 is connected to an electrical wire 224a which connects to acoustic signal processing circuitry such as IVUS processing circuitry.

The electrical pulses used to drive an ultrasound transducer and the pulses generated by the ultrasound transducer are transmitted between wire 224a and wire 224b using the electric fields generated by the two rings as a bridge for wireless signal transmission by induction. In one embodiment, the thickness of the gap between the two coils is between about 20 microns and about 200 microns. In one embodiment, the thickness of the gap between the two coils is greater than or equal to about 20 microns. In one embodiment, the thickness of the gap between the two coils is between about 20 microns and about 100 microns.

In various embodiments, the respective coils 228 in each respective ring 226, 227 have an equal number of turns or a ratio of turns to adjust for the impedance or voltage output of the acoustic data collection subsystem of the data collection probe. One or both of these coils 228 can also have a center tap. This center tap or connection to a coil winding provides access to the common mode of the signal lines. Since the image data collection probes are inserted into the patient, although using a true ground connection to mitigate noise would be helpful there are risks that such a true ground connection could lead to grounding of a patient during one or more procedures. The center tap connections to one of the plurality of windings such as the rotating windings or coil disposed in the PIU can provide a virtual ground which facilitates patient safety while simultaneously reducing or preventing common mode noise in the signal lines used to drive an acoustic element or another electrical component of a probe.

An optical path defined by one or more optical fibers is coaxial with the center of rotation of rotary joint 200. In one embodiment, the optical path includes a rotatable optical fiber 229*a* and a stationary optical fiber 229*b* separated by a small gap 229*c*. The gap 229*c* is formed using an optical coupler such as a fiber optic rotary joint. The rotatable fiber 229*a* connects into the rotatable optical connector 211 which can include a connector plate or support 211*a*, and the stationary fiber 229*b* and 223 connects into an optical signal processing system such as an OCT imaging engine. An outer housing 222 is also show with the rotor and stator disposed therein. Channel 212 can be formed in the outer housing 222 in one embodiment. A bearing pair 225 having an inner race facing the optical fibers 229*a*, 229*b* and an outer race facing the rotor 219 is shown. Rotatable fiber 229*a* is coupled to rotor 219 such that both rotate in a synchronized manner during one or more phases of a pullback. Various shaped channels corresponding to a space within housing 222 are shown as the cavity 250 disposed between the connector 211 and the rotor 219 and outer housing 222.

As shown in FIG. 6B, a stationary support 220 is used in conjunction with the stator 215. The fiber 229*b* and the bearing pair 225 are held stationary by stator 220. The stationary support 220 bears a portion of the load associated with stator 215. In turn, stator 215 is attached to bearing pair 225. The outer race of the bearing pair 225 provides a surface with respect to which such surface the rotor 219 rotates upon. The rotor 219, which can have a cup-shaped or other configuration, is rotatably disposed relative to the stator 215. The stator 215 defines a stator bore within which fibers 229*c* and 229*b* can be disposed along with an optical coupler to couple light between each respective fiber segment over a gap 229*c*. In one embodiment, wire 224*b* continues through channel 212 to connect to ring 227. Alternative arrangements of the relative order of the rotatable and stationary parts are possible. In general, in each such embodiment the electrical rotary joints are configured to define a hollow core or channel to allow positioning of an optical fiber and a stator. In one embodiment, each stator and rotor used in the PIU define a bore through which an optical fiber segment can be slidably disposed. FIGS. 12B and 12C show additional views of FIG. 6B.

Catheter Body

Figure 7:
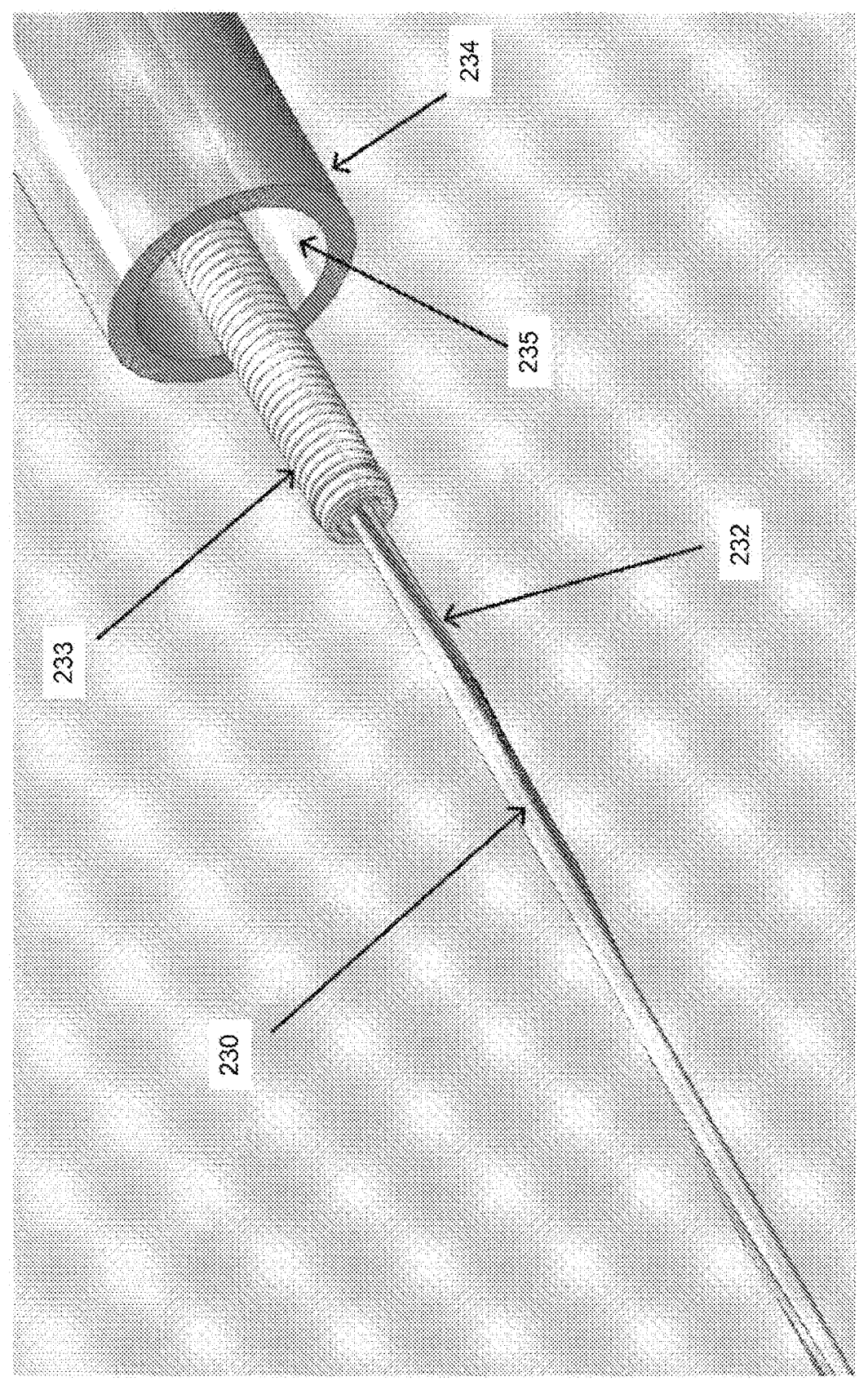
FIG. 7 is a perspective diagram of an embodiment of a catheter in accordance with an illustrative embodiment of the invention.

FIG. 7 shows a perspective diagram of the catheter or data collection probe body. The rotatable imaging core of the catheter body includes a central optical fiber 230 helically wrapped with electrical wires 232 and encased by a torque cable 233. In FIG. 7 the torque wire is shown in a truncated form and would typically extend along the optical fiber section which is shown in an exposed state. This arrangement maintains rotational symmetry, aligns the optical fiber 230 to a combination rotary joint, such as, for example, described and depicted herein, and allows sufficient torque transmission while maintaining the bending flexibility of the catheter.

In one embodiment, the rotatable imaging core is slidably disposed within the stationary catheter sheath 234. This allows the imaging core to spin and be pulled back into the sheath 234 while imaging a sample such as a blood vessel, thereby allowing the catheter sheath to protect the delicate vessel from the moving imaging core. To facilitate optical and acoustic energy transmission as well as providing vibrational damping, the annular space 235 between the torque cable and the sheath 234 is filled with saline, contrast or other suitable material to purge the air which poorly transmits acoustic signals.

Pullback Section

Figure 8A:
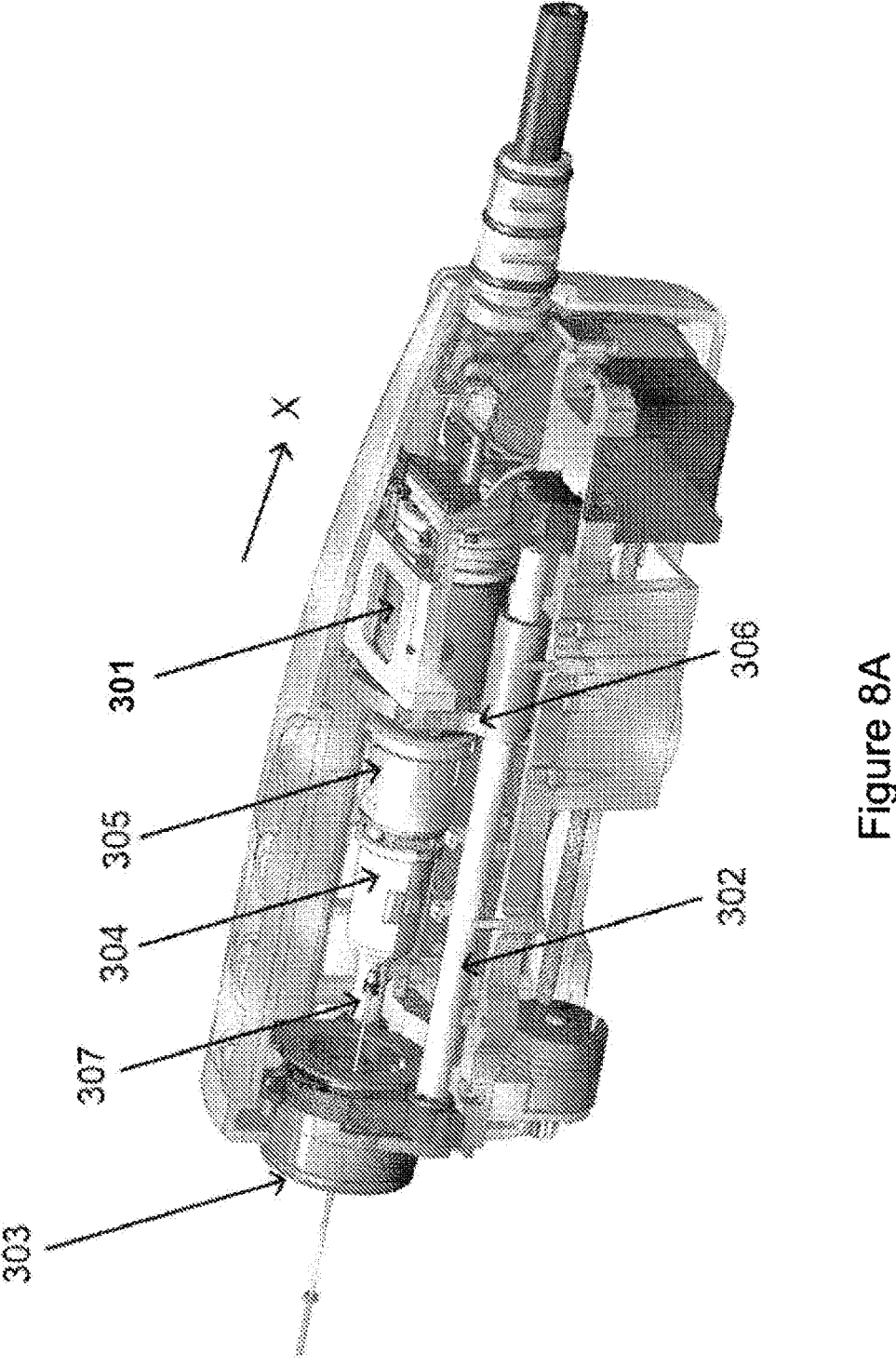
FIG. 8A is an open perspective of an embodiment of a PIU in accordance with an illustrative embodiment of the invention.

During the combination imaging of the tissue, the PIU provides relative linear motion between the stationary catheter sheath 234 and the spinning imaging core to pullback the imaging core. FIG. 8A shows an embodiment of a PIU capable of providing this linear motion. The linear motion is obtained by mounting a combination rotary joint 301 coupled to a carriage 306 onto a linear rail system 302. The catheter sheath and outer housing (not shown) is rigidly attached to a stationary point 303 on the PIU. The imaging core connector 304 is attached to the spinning connector end 305 of the rotary joint. As the carriage 306 with the rotary joint is pulled back, (Arrow X) the imaging core slides relative to the catheter sheath.

Figure 8B:
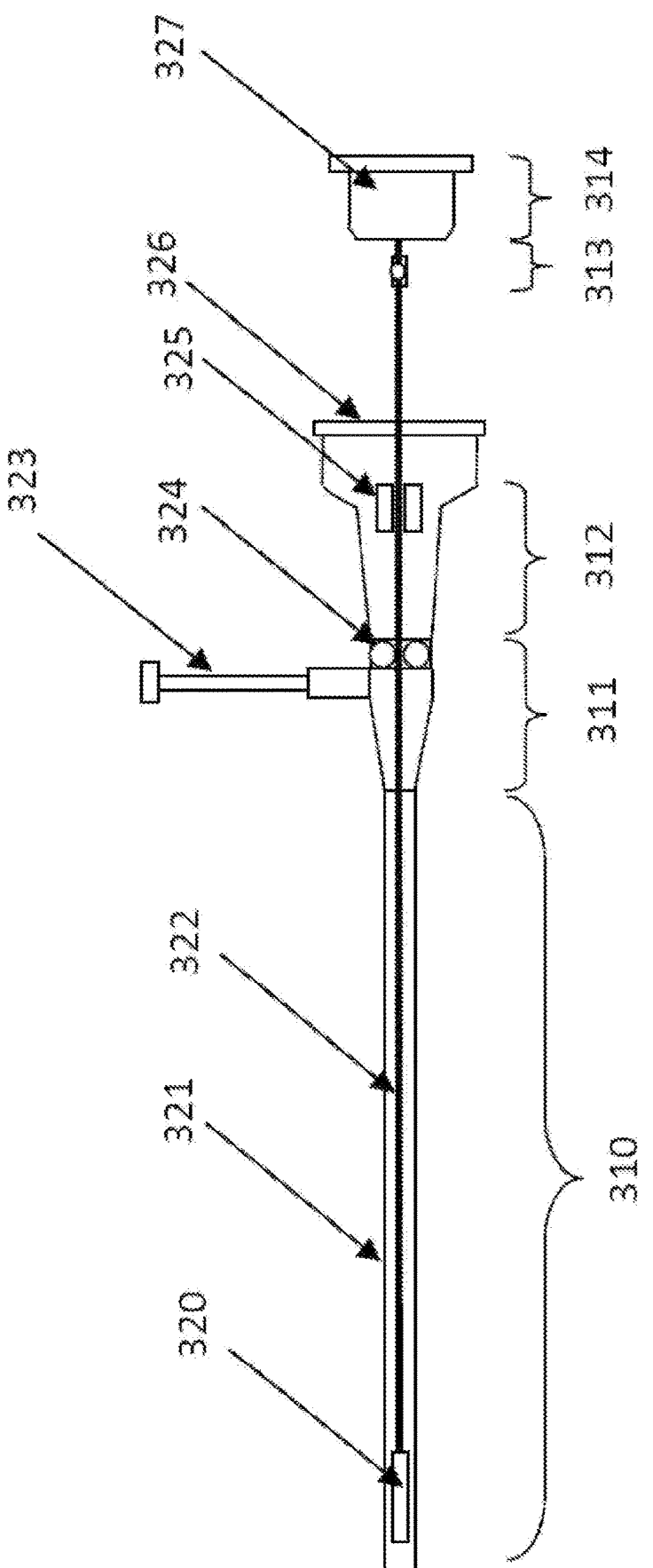
FIG. 8B is a cross-sectional schematic diagram of a catheter pull-back section m accordance with an illustrative embodiment of the invention.

Additionally in this region a seal or other mechanism is used to isolate the PIU from the catheter purging process. This region near the seal can also include a section designed to break-away when subject to excessive forces as a safety feature to prevent the image core from continuing to rotate when the probe end is bound. FIG. 8B depicts an embodiment of the combination catheter pullback section such that various sections and their related features are described.

The different zones of the catheter perform different functions or have different characteristics. For example, the catheter can be divided into five discrete sections. The first section 310 includes the portion that is inserted into the body, including the stationary catheter 321, the rotatable imaging sensors 320 and the rotatable catheter body 322 as described herein.

The fourth section 313 is break away safety area that will mechanically isolate the image core from the rotary driver if a set torque level is exceeded (alternatively this can be located anywhere proximal to the human insertion point).

The fifth section 314 is the imaging core connector 327 which will be described in detail in the paragraph below.

Catheter Connector

The catheter has human blood contact and is typically a sterile single use device. In contrast, the PIU does not have significant blood contact and is much more expensive than the catheter. As a result a PIU is typically reused and remains unsterile during use. A disposable connector is used to mate these two parts. This connector needs to have high reliability and maintain catheter sterility during engagement. There are four subsystems or components that are being connected by the disposable connector.

The first is the mechanical connection of the catheter sheath to the stationary PIU body which is described in the paragraph above. The second is the mechanical connection of the imaging core to the rotatable/translating carriage containing the combination rotary joint. The third is an optical connection between the fiber optic in the catheter and the fiber optic rotary joint. The fourth is an electrical connection between one or more signal wires of a transducer-based sensor for acoustic imaging in the imaging core and the electrical rotary joint.

Figure 9:
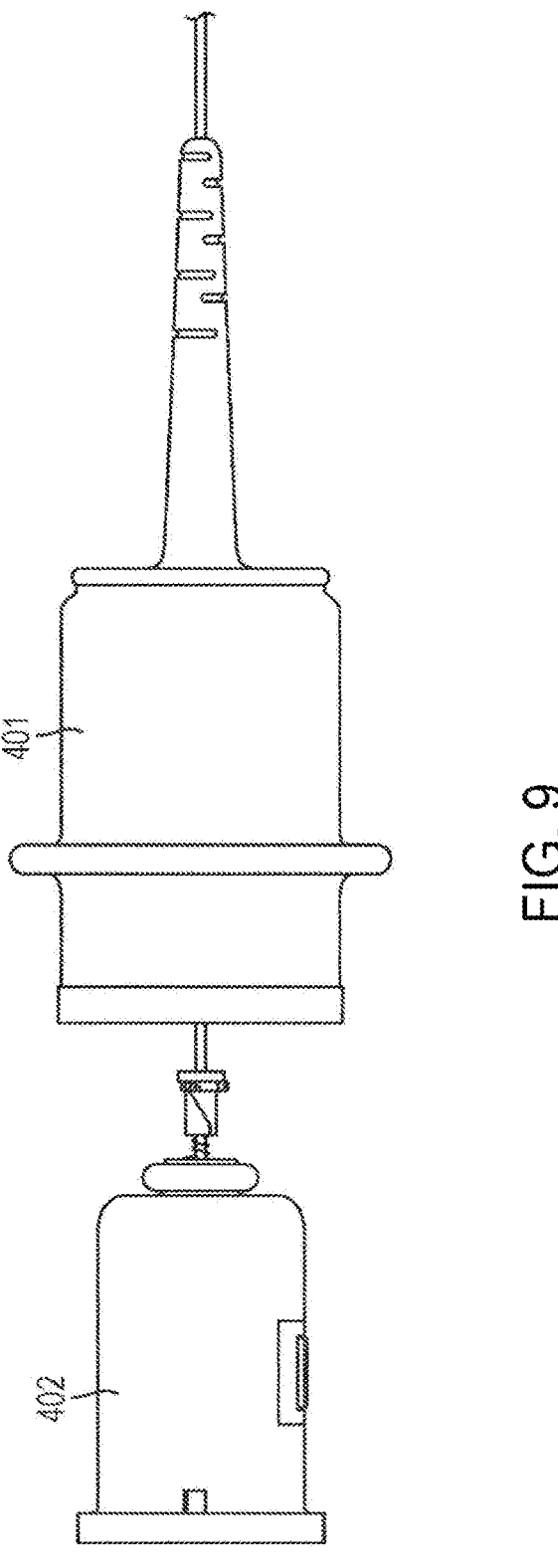
FIG. 9 is a photograph of an imaging core connector in accordance with an illustrative embodiment of the invention.

Considering these functions in more detail, an embodiment of the connector is shown in FIG. 9. For clarity, in this figure the imaging core connector 402 is shown fully withdrawn from the outer shell 401. During actual connector engagement the imaging core connector 402 is fully nested inside of the outer shell 401. To engage the connector, the operator grasps the sterile outer shell 401 of the catheter and mechanically interlocks it into a port 303 (FIG. 8A) on the non-sterile PIU. The PIU may be either be covered with a sterile bag with an opening allowing access to this port or the operator must take care to avoid touching the non-sterile PIU. Once this mechanical interlock is detected by the PIU, it automatically engages the optical and electrical connectors of the probe with the counterpart connectors in the PIU. This automatic engagement eliminates the need for the operator to make more interconnects between sterile and non-sterile parts. Specifically, the PIU carriage approaches the inner (imaging core) connector with the spinning PIU connector to mechanically locate and rotationally engage the inner (imaging core) catheter connector.

Once the catheter connector is rotationally engaged, the PIU connector further advances to sequentially engage the optical and electrical connectors and finally to mechanically lock the inner catheter connector to the PIU. Disconnecting the catheter from the PIU is done in a similar manner. During disconnection, the sterile operator need only touch the still sterile outer connector. In one embodiment, it is desirable to maintain a sterile state in the event of a follow on procedure such as another pullback or a stent removal or stent placement.

To facilitate reliable electrical and optical connection, these interconnects have a swiping, sliding or spring loaded action to bring the electrical couplers and the optical couplers into alignment and solid contact. The optical and electrical connectors in the PIU that engage the disposable imaging probe are configured to have a continuous biasing force on one or both of an optical connector or an electrical connector such that it remains able to receive and connect with a corresponding optical and electrical connector in the probe. In one embodiment, the PIU is designed with a double ended sacrificial interconnect. This allows worn or damaged electrical and/or optical connectors to be easily switched out without replacing the entire PIU.

Figure 10A:
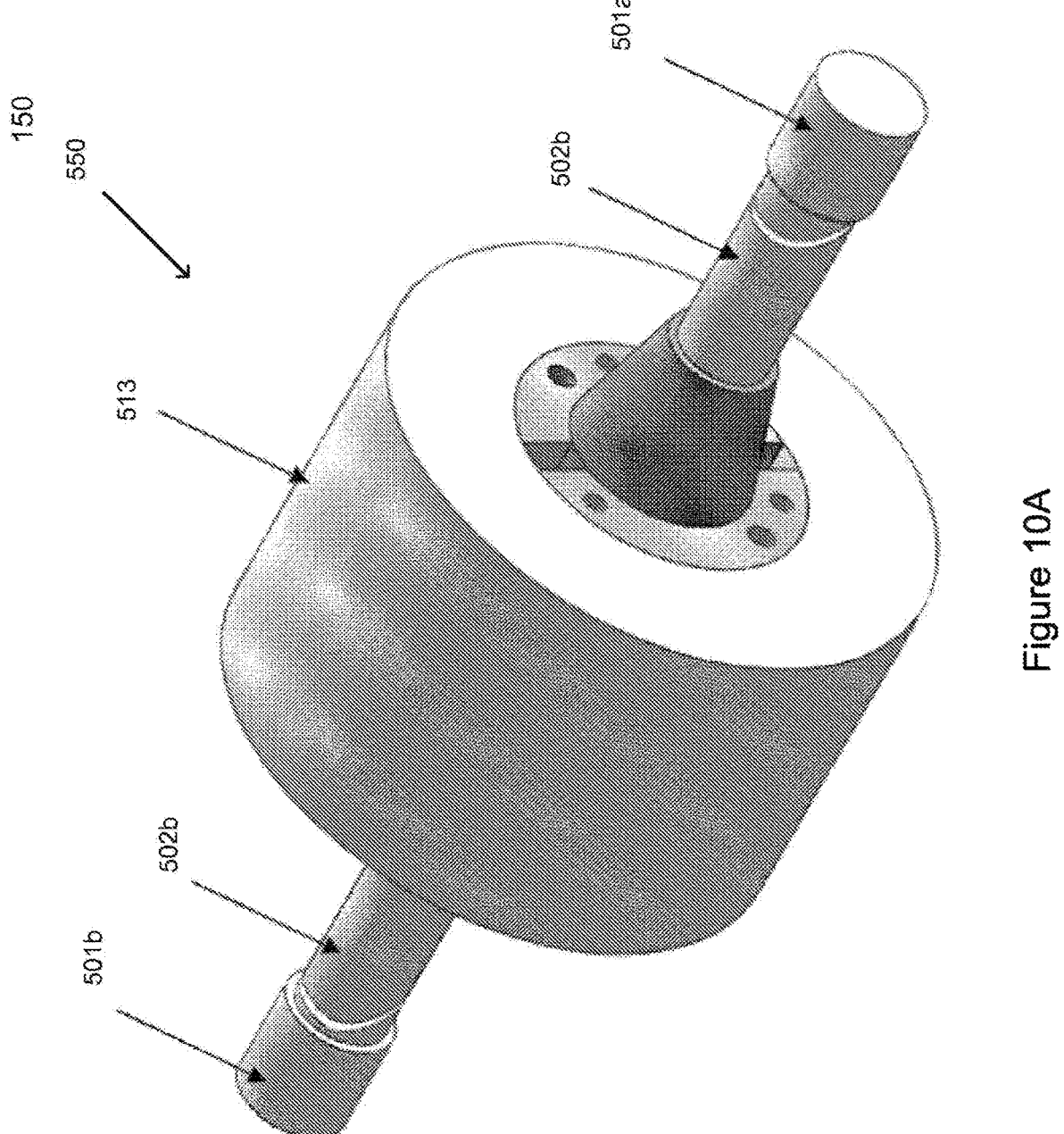
FIG. 10A is another combination rotary joint m accordance with an illustrative embodiment of the invention.

As shown in FIG. 10A, another rotary joint 550 is depicted according to an embodiment of the invention. The embodiment shown has one rotatable end 501a, one stationary end 501b, preloaded ball bearing pair 510, and a rotary joint housing 513. One rotatable end 501a is aligned with a rotatable portion of a transformer and the stationary end 501b is aligned with a stationary portion of a transformer assembly.

Figure 10B:
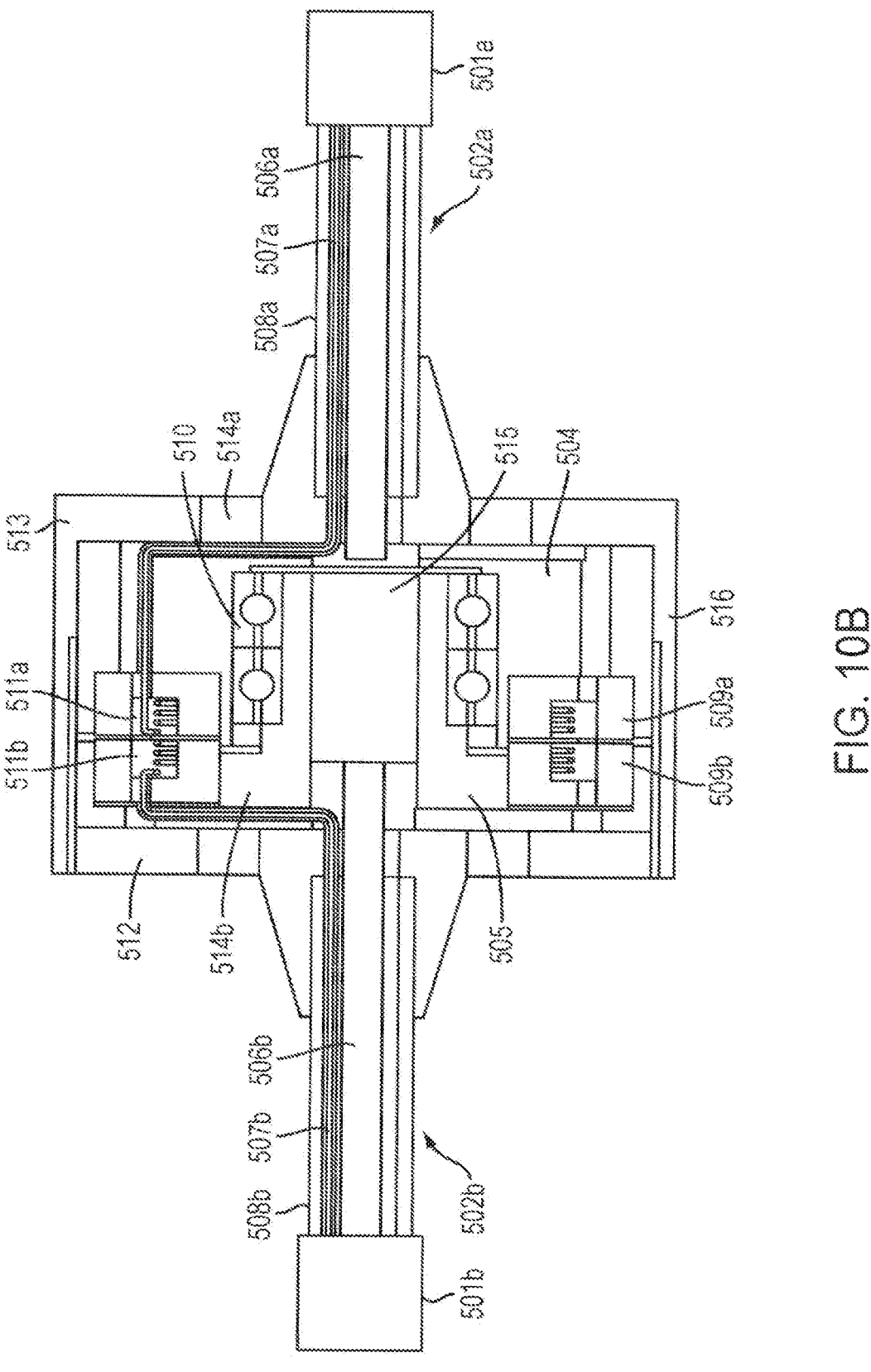
FIG. 10B is a cross-sectional diagram of the combination rotary joint of FIG. 10A.

Additional details of the rotary joint of FIG. 10A are shown in the cross-sectional view of FIG. 10B. The rotatable end includes a rotor 505 which mechanically orients all rotatable components around the axis of rotation. Within an annular pocket or cavity defined by rotor 505 a rotatable electrical transformer section or component is affixed. The rotatable transformer portion or component includes a plurality of conductive windings. The windings can be disposed in a ferrite core 509b as a plurality of concentric wire coils 511b embedded in the ferrite core 509b. The winding are annularly disposed relative to the optical fiber 506b and optical components 515. Optical components 515 can include a fiber optical coupler configured to align a rotatable fiber segment (not shown) which would be entering the PIU from the left side of the figure with a stationary fiber segment (not shown) which would be entering the PIU from the right side of the figure. An air gap would be disposed between the endface of each of the two fibers with optical image data and incident light crossing the gap.

A rotatable optical fiber 506b and optical components 515 are affixed concentrically within a bore or channel disposed along the central axis of the rotor 505. A rotary channel 514b is also formed in or defined by the rotor 505 to allow the electrical transmission lines 507b to exit the rotor 505 and be included in a cable 502b. Cable 502b provides a jacket for optical fiber 506b and the electrical signal transmission lines 507b. The cable 502 also provides strain relief for the components disposed therein. The cable 502b connects to one or more rotary connectors 501b which are used to transmit and receive signals through the electrical signal transmission lines 507b and the optical fiber 506b.

Still referring to FIG. 10B, the stationary end includes a stator 504 which mechanically orients all the stationary components around the same. A rotor 505 configured to rotate relative to the stator 504 is shown. A stationary electrical transformer section or component is annularly disposed and concentric to the axis of rotation of the joint 550. The stationary electrical transformer component is disposed in an annular pocket or cavity defined by the stator 504. The stationary transformer component includes a ferrite core 509a and concentric wire coils 511a embedded in the ferrite core 509a.

A stationary optical fiber 506a is affixed concentrically is a bore or channel disposed along the central axis of the stator 504. A stationary channel 514a for the electrical signal transmission lines is defined by the stator 504. The channel 514a is configured to allow the electrical transmission lines 507a to exit the stator 504 and be included in a cable 502a. Cable 502a provides a protective jacket and also provides strain relief for the optical fiber 506a and the electrical signal transmission lines 507a. The cable 502a connects to one or more stationary connectors 501a. Such as connector 501a is used to allow signals to be transmitted and received through the electrical signal transmission lines 507a and the optical fiber 506a.

The rotatable and stationary ends interface mechanically through the core bearing pair 510. The core bearing pair 510, positioned at the interface of the rotor 505 and stator 504, allow rotation of the rotary end components while maintaining concentricity of the rotor 505 to the stator 504. The stationary end is positioned within the rotary joint housing 513 and compression fit or adhered to ensure concentricity of the stator 504 to the rotary joint housing 513. The rotary joint housing 513 and the rotor 505 are designed to provide a gap between the rotor 505 and the rotary joint housing 513 to allow for free rotation.

The concentric wire coils 511a and 511b of the electrical transformer can have an equal number of turns or a ratio to adjust the impedance or voltage output. One or both of these coils can also have a center tap allowing access to the common mode of the signal lines. The rotatable electrical transformer component and the stationary electrical transformer component are separated by a small gap 516. The gap 516 being in close proximity to the core bearing pair 510 is susceptible to EMI created by the motion of the components in the core bearing pair. If the EMI from the bearing pair 510 is significant, the gap 516 can be shielded by extending the body of the stator 504 such that the gap 516 is covered by the stator 504.

Accordingly, in one embodiment, the width of the stator which now terminates before gap 516 would extend over the gap towards coil 509b. Thus, if the stator has a cylindrical wall thickness that terminates before the gap that thickness can be extended so one end face of the stator extends beyond the gap. If the material used for the body of the stator 504 does not possess good EMI shielding properties the extension can be plated with a shielding material. The stator extension is configured to leave a gap between the stator 504 and rotor 505 allowing the free motion of the rotatable end.

Figure 11A:
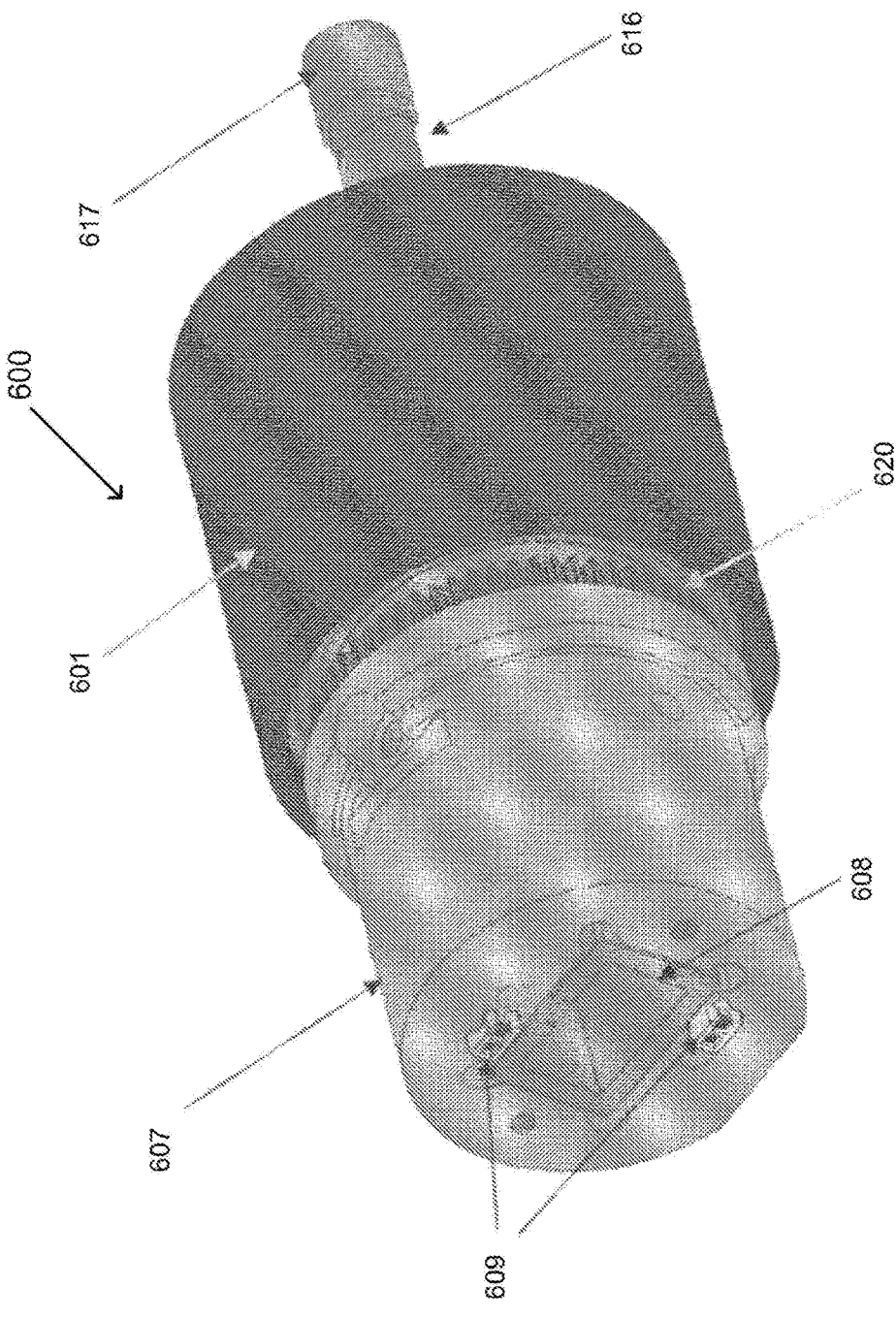
FIG. 11A is yet another combination rotary joint embodiment in accordance with an illustrative embodiment of the invention.
Figure 11B:
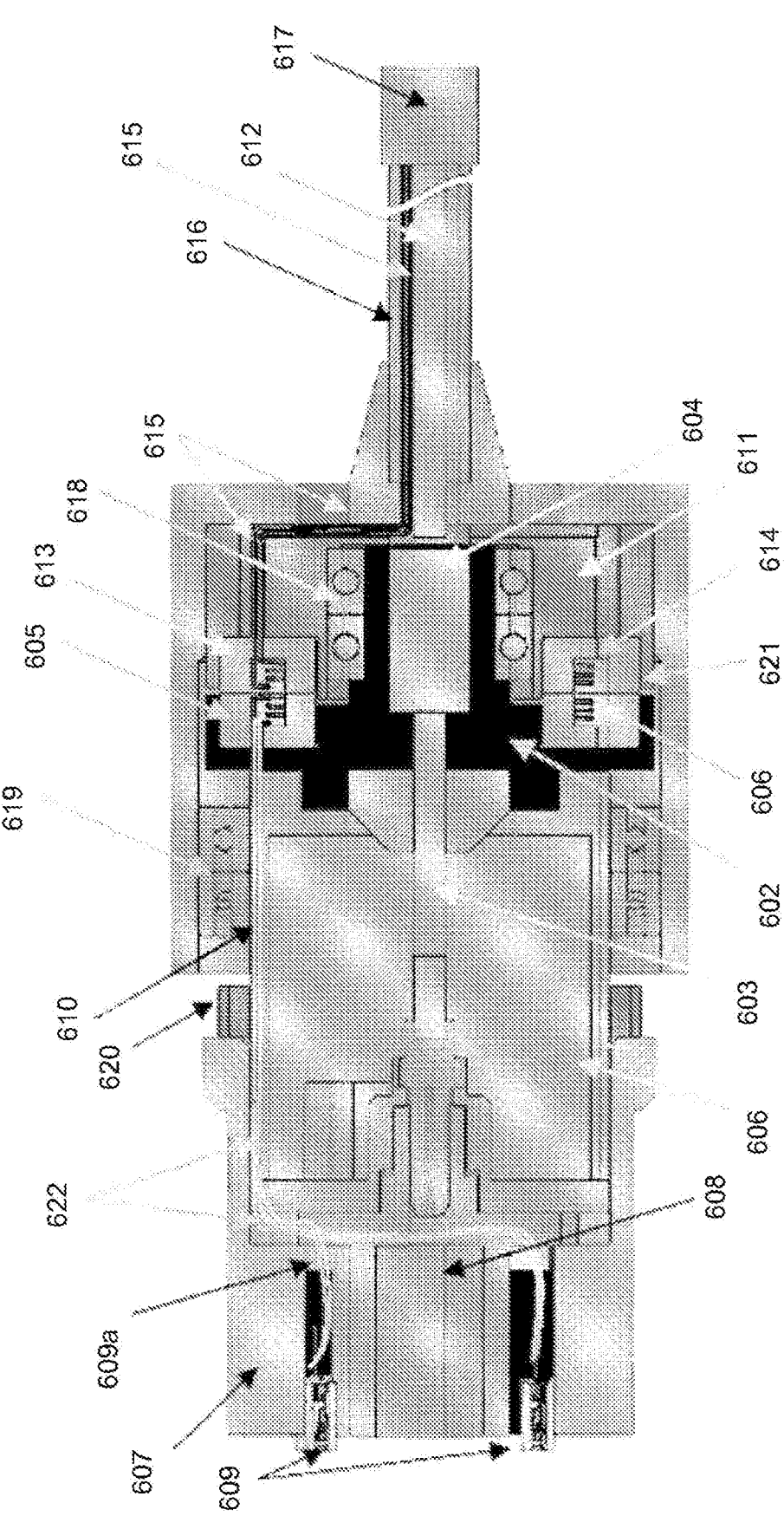
FIG. 11B is a cross-sectional diagram of the combination rotary joint of FIG. 11A.

As shown in FIG. 11A, another rotary joint 600 is depicted according to an embodiment of the invention. In this embodiment the combined rotary joint has one rotatable end, one stationary end, preloaded ball bearing pairs 618 and 619, and a rotary joint housing 601. Additional details of the rotary joint of FIG. 11A are shown in the cross-sectional view of FIG. 11B. The rotatable end includes a rotor 602 which mechanically orients all rotatable components around the axis of rotation. Within an annular pocket or cavity defined by the rotor 602 a rotatable electrical transformer component is affixed. The rotatable transformer component includes a ferrite core 605 and concentric wire coils 606 embedded in the ferrite core 605. The rotatable transformer component is annularly disposed relative to the optical fiber 603 and optical components 604.

A rotatable optical fiber 603 and optical components 604 are affixed concentrically to a bore or channel disposed along the central axis of the rotor 602. A rotatable connector extension 606 is affixed to the rotor and is compression fit over a protuberance in the rotor 602. This maintains concentricity of 606 to the axis of rotation with respect to rotor and the stator.

Mounted onto the rotatable connector extension 606 is the rotatable fiber connector 608. A connector hub 607 which houses the rotatable electrical connectors 609 is mounted onto the rotatable connector extension 604 and around the rotatable fiber connector 608. The connector hub 607 can mechanically balance the rotatable components. Connector hub 607 corresponds to 145 in FIG. 3B. A rotatable channel 622 is formed in the rotatable connector extension 606 and the connector hub 607. Rotatable channel 622 is arranged and configured such that the electrical signal transmission lines 610 can travel to the rotatable electrical connectors 609 without interference from the support bearing pair 619 or the mechanical drive component 620.

The stationary end includes a stator 611 which mechanically orients all the stationary components around the same axis. A stationary electrical transformer component is affixed to an annular pocket or cavity defined by or formed in the stator 611. This stationary transformer component is annularly disposed and concentric to the axis of rotation. The stationary transformer component includes a ferrite core 613 and concentric wire coils 614 embedded in the ferrite core 613. A stationary optical fiber 612 is affixed concentrically to a bore or channel along the central axis of the stator 611.

A stationary channel for the electrical signal transmission lines 615 is formed in or defined by the stator 611 to allow the electrical transmission lines 615 to exit the stator 611 and be included in a cable 616. Cable 616 provides a jacket and strain relief for the optical fiber 612 and the electrical signal transmission lines 615. Along the cable 616, a connection to one or more stationary connectors 617 is made. This connection allows signals to be transmitted and received through the electrical signal transmission lines 615 and the optical fiber 612.

The rotatable and stationary ends interface mechanically through two pairs of preloaded ball bearings, the core bearing pair 618 and the support bearing pair 619. The core bearing pair 618, positioned at the interface of the rotor 602 and stator 611, allow rotation of the rotary end components while maintaining concentricity of the rotor 602 to the stator 611. The support bearing pair 619, positioned at the interface of the rotatable connector extension 606 and the rotary joint housing 601, provides support for the load of the rotatable end while maintaining concentricity of the rotatable end to the rotary joint housing 601 and therefore to the stationary end.

The stationary end is positioned within the rotary joint housing 601 and secured with a tight fit to ensure concentricity of the stator 611 to the rotary joint housing 601. The rotary joint housing 601 and the rotor 602 are designed to provide a gap between the rotor 602 and the rotary joint housing 601 to allow for free rotation. The rotary joint housing 601 and the rotatable connector extension 606 are designed to leave a gap where the support bearing pair 619 will fit tightly. The rotary joint housing 601 is designed to leave exposed the rotatable electrical connectors 609 and the rotatable fiber connector 608. The rotary joint housing 601 also includes an engaging or drivable component 620 such as a gear. Various types of such drive components or engagement components 620 can be used in other embodiments.

The concentric wire coils 606 and 614 of the electrical transformer can have an equal number of turns or a ratio to adjust the impedance or voltage output. One or both of these coils can also have a center tap allowing access to the common mode of the signal lines. The rotatable electrical transformer section or component and the stationary electrical transformer section or component are separated by a small air gap 621. The gap 621 being in close proximity to the core bearing pair 618 and the support bearing pair 619 could be susceptible to electromagnetic interference EMI created by the motion of the components in the core bearing pair.

If the EMI from the bearing pairs 618 and 619 is significant, the gap can be shielded by extending the body of the stator 611 such that the gap 621 is covered by the stator 611. Alternatively, if the material used for the body of the stator does not possess suitable EMI shielding properties the extension can be plated with a shielding material. The extension will be designed to leave a gap between the stator 611 and rotor 602 allowing the free motion of the rotatable end.

Figure 12A:
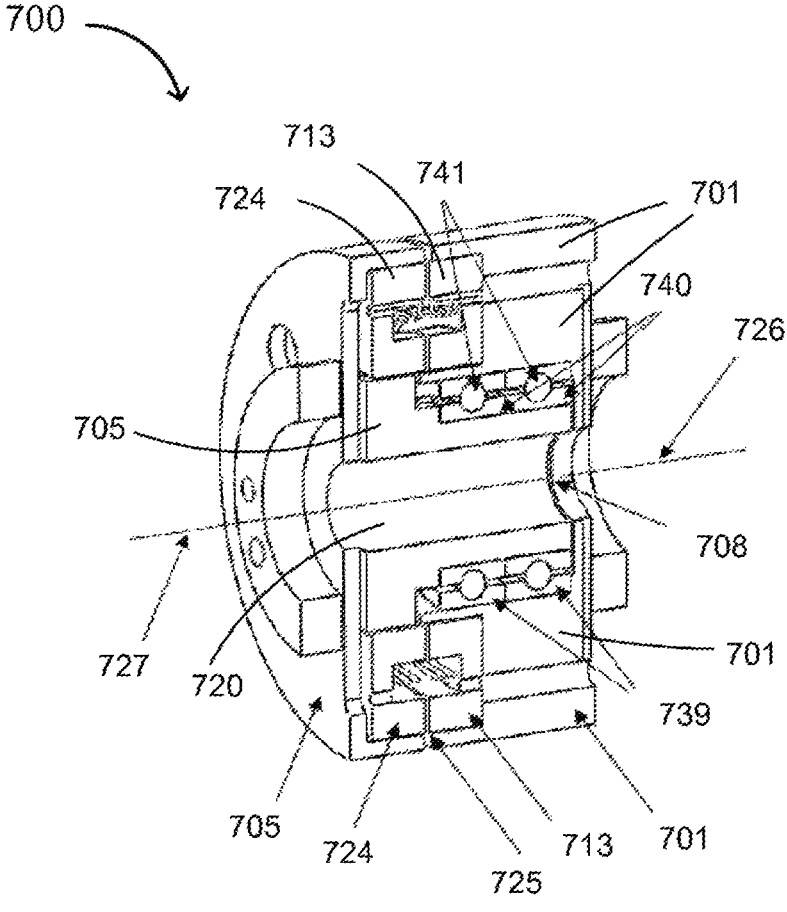
FIG. 12A is a schematic diagram of components of an interface device including rotatable components such as a rotor a rotatable plurality of conductive windings in accordance with an illustrative embodiment of the invention.
Figures 12B, 12C:
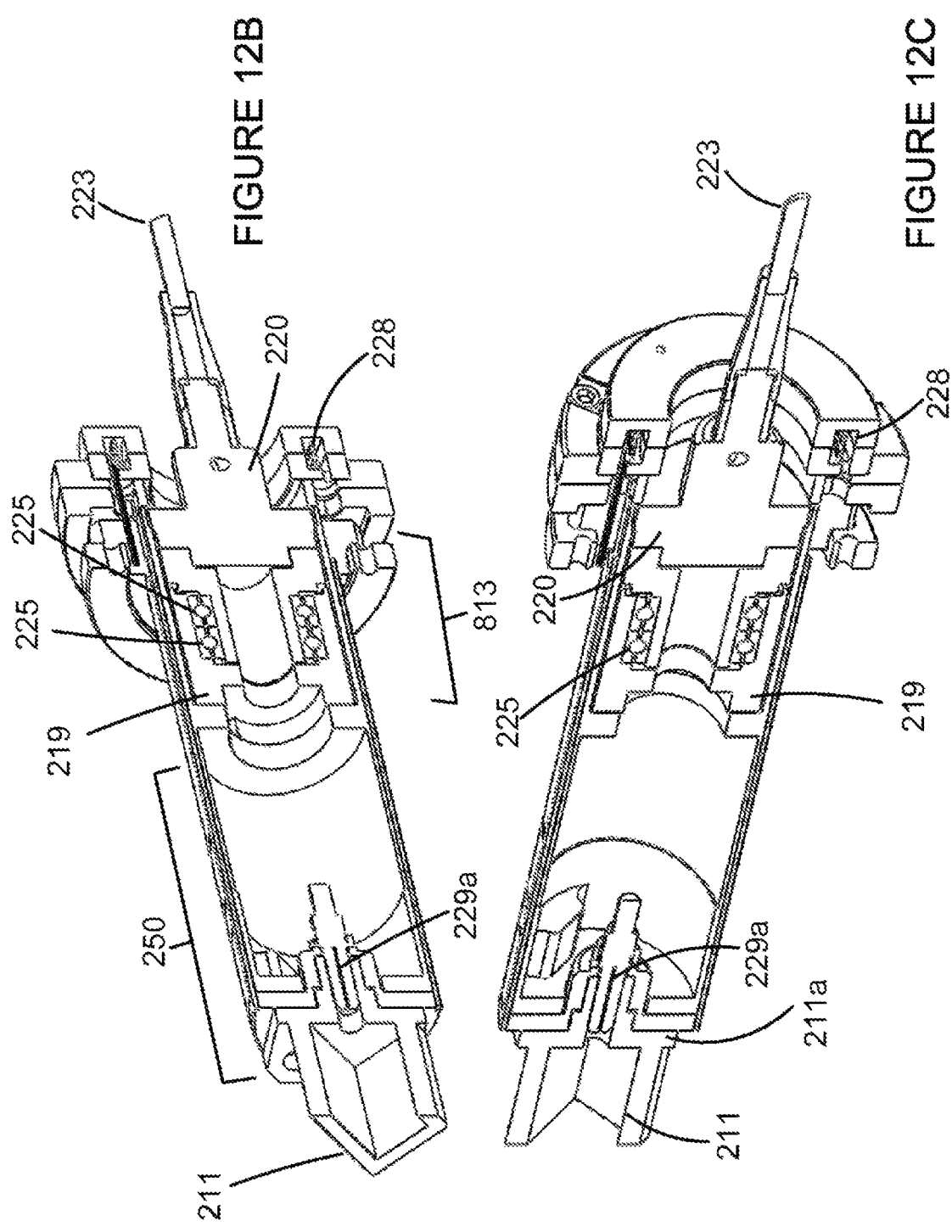
FIGS. 12B and 12C are two perspective views of the components of FIG. 6B along with additional connectors used in an exemplary interface device in accordance with an illustrative embodiment of the invention.

Various components of an interface device are shown in the cross-sectional perspective view of FIG. 12A. Specifically, a stator 701 is shown relative to a rotor 705. The stator 701 is configured to define a cavity in which one or more portions of a rotor 705 are disposed. A stator bore is sized to receive a bearing pair which includes bearing pair stationary races 739 and bearing pair rotatable races 740. Although reference is made to bearing pairs, in one embodiment one bearing or another load bearing element suitable for facilitating rotor 705 movement relative to the stator 701 can be used.

The bearing pair balls 741 are disposed within the races of the bearing pair races 739, 740 as shown. Additionally, a stationary optical fiber 726 is disposed within a stator core 701. The stator 701 generally remains stationary. For example, it does not freely rotate relative to some of the other components shown. The stationary components such as the stator 701 and stationary optical fiber are disposed to the right of the gap 725 define, at least in part, by a rotatable transformer component or assembly 724 and a stationary transformer component or assembly 713.

The rotor 705 is rotatable and configured to rotate during one or more phases of a pullback. To provide coupling of the electrical signals used for an acoustic wave transducer as part of ultrasound imaging, a stationary transformer portion which includes a plurality of stationary windings can be implemented as show by the ferrite and wire coils 713. Similarly, a rotatable transformer portion which includes a plurality of rotatable windings can be implemented as show by the ferrite and wire coils 724. Either of the portions of the transformer can be separated by an electrical transformer air gap 725. In turn, just as the electrical system includes an arrangement of a stationary component and rotatable component so to do the optical elements which define sections of the sample arm of an interferometer. The rotatable optical fiber 727 sends and receives light via rotatable optical fiber 727 to stationary optical fiber 726.

In the description, the invention is discussed in the context of optical coherence tomography; however, these embodiments are not intended to be limiting and those skilled in the art will appreciate that the invention can also be used for other imaging and diagnostic modalities or optical systems in general.

The terms light and electromagnetic radiation are used interchangeably herein such that each term includes all wavelength (and frequency) ranges and individual wavelengths (and frequencies) in the electromagnetic spectrum. Similarly, the terms device and apparatus are also used interchangeably. In part, embodiments of the invention relate to or include, without limitation: sources of electromagnetic radiation and components thereof; systems, subsystems, and apparatuses that include such sources; mechanical, optical, electrical and other suitable devices that can be used as part of or in communication with the foregoing; and methods relating to each of the forgoing. Accordingly, a source of electromagnetic radiation can include any apparatus, matter, system, or combination of devices that emits, re-emits, transmits, radiates or otherwise generates light of one or more wavelengths or frequencies.

One example of a source of electromagnetic radiation is a laser. A laser is a device or system that produces or amplifies light by the process of stimulated emission of radiation. Although the types and variations in laser design are too extensive to recite and continue to evolve, some non-limiting examples of lasers suitable for use in embodiments of the invention can include tunable lasers (sometimes referred to as swept source lasers), superluminescent diodes, laser diodes, semiconductor lasers, mode-locked lasers, gas lasers, fiber lasers, solid-state lasers, waveguide lasers, laser amplifiers (sometimes referred to as optical amplifiers), laser oscillators, and amplified spontaneous emission lasers (sometimes referred to as mirrorless lasers or superradiant lasers).

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

What is claimed is:

1. A data collection system comprising:
   a disposable data collection probe; and
   a probe connector comprising an electrical connector and a counterbalance that is configured relative to one or more probe connector components to reduce rotational imbalance, wherein, the probe connector is configured to receive the disposable data collection probe, the disposable data collection probe comprising an ultrasound transducer and a rotatable optical fiber segment, and wherein the electrical connector is in electrical communication with the ultrasound transducer.

2. The data collection system of claim 1, further comprising a first section of a sample arm of an interferometer, the first section comprising a stationary optical fiber segment configured to transmit and receive light from a light source; and
   an optical rotary joint comprising an optical coupler configured to couple the stationary optical fiber segment to the rotatable optical fiber segment, wherein the rotatable optical fiber segment is a second section of the sample arm an interferometer.

3. The data collection system of claim 2, further comprising
   a stator defining a stator bore; and
   a rotor defining a rotor bore, wherein the stationary optical fiber segment is concentrically disposed in the stator bore, wherein the light is directed to image a blood vessel.

4. The data collection system of claim 3, wherein the rotor is at least partially disposed in the stator bore.

5. The data collection system of claim 3, wherein the stator is at least partially disposed in the rotor bore.

6. The data collection system of claim 3, further comprising an electrical rotary joint comprising
   a first annular ring defining a first annular opening and comprising a first conductive winding and
   a second annular ring defining a second annular opening and comprising a second conductive winding, wherein a first gap is defined between the first conductive winding and the second conductive winding and an elongate cavity is defined by the first and second annular openings,
   wherein the optical rotary joint and the electrical rotary joint are coaxial and the light passes through the elongate cavity to the rotatable optical fiber segment of the disposable data collection probe.

7. The data collection system of claim 6, wherein the optical coupler is disposed within the elongate cavity.

8. The data collection system of claim 7, wherein the first conductive winding is disposed in a first ferrite ring and the second conductive winding is disposed in a second ferrite ring, wherein the first and second ferrite rings are parallel.

9. The data collection system of claim 6, wherein the first gap ranges from about 20 microns to about 100 microns.

10. The data collection system of claim 6, wherein a second rotatable optical fiber segment and the optical rotary joint are at least partially disposed in the elongate cavity and one or more of the conductive windings are annularly disposed around the optical rotary joint.

11. The data collection system of claim 6, wherein a ratio of a number of turns in the first conductive winding to a number of turns in the second conductive winding ranges from 0.25 to 4.

12. The data collection system of claim 6, wherein the optical rotary joint and the electrical rotary joint are arranged along a common axis of rotation.

13. The data collection system of claim 6, wherein the first conductive winding is rotatable and the second conductive winding is stationary.

14. The data collection system of claim 13, further comprising a center tap connection with one or more stationary windings configured to reduce common mode noise.

15. The data collection system of claim 6, wherein the second conductive winding is rotatable windings and the rotatable optical fiber segment and rotatable windings are connected to the rotor.

16. The data collection system of claim 1, further comprising a motor configured to rotate the rotatable optical fiber segment.

17. The data collection system of claim 1, wherein the probe connector comprises a rotatable electrical wire.

18. The data collection system of claim 17, further comprising a cylindrical tube comprising a cylindrical surface defining an elongate channel configured to receive the rotatable electrical wire or a conductor in electrical communication with the electrical rotatable wire.

19. The data collection system of claim 1, further comprising a connector hub configured to rotationally balance one or more rotatable components.

20. The data collection system of claim 1, wherein the rotatable optical fiber segment is configured to transmit light from a light source and receive light and a probe body.

* * * * *